US008876720B2

(12) United States Patent
Vezina

(10) Patent No.: US 8,876,720 B2
(45) Date of Patent: Nov. 4, 2014

(54) PERIPHERAL ULTRASOUND DEVICE PROVIDING PIVOTAL ADJUSTMENT OF AN IMAGING MECHANISM ABOUT TWO AXES

(75) Inventor: Daniel Vezina, Park City, UT (US)

(73) Assignee: Guardsman Scientific, Inc., Park City, UT (US)

( * ) Notice: Subject to any disclaimer, the term of this patent is extended or adjusted under 35 U.S.C. 154(b) by 1316 days.

(21) Appl. No.: 12/646,617

(22) Filed: Dec. 23, 2009

(65) Prior Publication Data
US 2010/0168577 A1 Jul. 1, 2010

Related U.S. Application Data

(63) Continuation-in-part of application No. 12/536,247, filed on Aug. 5, 2009, now Pat. No. 8,348,847.

(60) Provisional application No. 61/086,254, filed on Aug. 5, 2008, provisional application No. 61/140,767, filed on Dec. 24, 2008, provisional application No. 61/224,621, filed on Jul. 10, 2009.

(51) Int. Cl.
*A61B 8/00* (2006.01)
*A61B 5/02* (2006.01)
*G01S 7/52* (2006.01)
*G06F 19/00* (2011.01)
*A61B 8/06* (2006.01)
*A61B 8/08* (2006.01)
*A61B 6/00* (2006.01)

(52) U.S. Cl.
CPC ............... *A61B 8/00* (2013.01); *A61B 8/4461* (2013.01); *A61B 8/4236* (2013.01); *A61B 8/4209* (2013.01); *A61B 8/46* (2013.01); *A61B 5/02028* (2013.01); *G01S 7/52079* (2013.01); *A61B 8/0883* (2013.01); *G06F 19/3418* (2013.01); *A61B 8/06* (2013.01); *A61B 6/503* (2013.01); *A61B 8/4281* (2013.01); *A61B 8/4466* (2013.01)
USPC ........................................................ 600/459

(58) Field of Classification Search
None
See application file for complete search history.

(56) References Cited

U.S. PATENT DOCUMENTS

| 4,165,270 A | 8/1979 | Ost |
| 4,305,207 A | 12/1981 | Lantz |
| 4,343,092 A | 8/1982 | Wahl et al. |
| 4,827,943 A | 5/1989 | Bornn et al. |

(Continued)

FOREIGN PATENT DOCUMENTS

| EP | 0607490 | 7/1994 |
| JP | 05337108 | 12/1993 |

OTHER PUBLICATIONS

International Search Report and Written Opinion, PCT/US2009/052850, Sep. 29, 2009, 11 pages.

(Continued)

*Primary Examiner* — Unsu Jung
*Assistant Examiner* — Amanda Lauritzen Moher
(74) *Attorney, Agent, or Firm* — Polsinelli PC

(57) ABSTRACT

A device for acquiring ultrasound-generated data from a patient including a securing system and a probe configured for connection to the securing system, the probe including a base having an interfacing surface, an imaging mechanism adjustable relative to the base and configured to send and receive ultrasound signals along an imaging direction, and an adjustment mechanism configured to adjust the imaging mechanism relative to the base thereby adjusting the imaging direction.

14 Claims, 18 Drawing Sheets

(56) References Cited

U.S. PATENT DOCUMENTS

| | | | |
|---|---|---|---|
| 4,857,836 | A | 8/1989 | Soelkner |
| 4,908,568 | A | 3/1990 | Soelkner |
| 4,947,853 | A | 8/1990 | Hon |
| 5,022,410 | A | 6/1991 | Hall |
| 5,070,880 | A | 12/1991 | Gomez et al. |
| 5,394,877 | A | 3/1995 | Orr et al. |
| 5,469,852 | A | 11/1995 | Nakamura et al. |
| 5,598,845 | A * | 2/1997 | Chandraratna et al. ........ 600/459 |
| 5,634,468 | A | 6/1997 | Platt et al. |
| 5,704,352 | A | 1/1998 | Tremblay et al. |
| 5,740,804 | A | 4/1998 | Cerofolini |
| 5,771,896 | A | 6/1998 | Sliwa, Jr. et al. |
| 5,807,268 | A | 9/1998 | Reeves et al. |
| 5,947,961 | A | 9/1999 | Netherly |
| 6,031,383 | A | 2/2000 | Streib et al. |
| 6,124,723 | A | 9/2000 | Costello |
| 6,126,636 | A | 10/2000 | Naka |
| 6,132,371 | A | 10/2000 | Dempsey et al. |
| 6,248,101 | B1 | 6/2001 | Whitmore, III |
| 6,261,231 | B1 | 7/2001 | Damphousse et al. |
| 6,285,180 | B1 | 9/2001 | Pas |
| 6,577,893 | B1 | 6/2003 | Besson et al. |
| 6,653,825 | B2 | 11/2003 | Munniksma |
| 7,215,991 | B2 | 5/2007 | Besson et al. |
| 7,244,230 | B2 | 7/2007 | Duggirala et al. |
| 8,038,622 | B2 * | 10/2011 | Abraham ...................... 600/459 |
| 2002/0077547 | A1 | 6/2002 | Sluis |
| 2002/0120310 | A1 | 8/2002 | Linden et al. |
| 2003/0187362 | A1 | 10/2003 | Murphy et al. |
| 2003/0220578 | A1 | 11/2003 | Ho et al. |
| 2004/0006278 | A1 | 1/2004 | Webb et al. |
| 2004/0015081 | A1 | 1/2004 | Kramer et al. |
| 2005/0139213 | A1 | 6/2005 | Blike |
| 2005/0157888 | A1 | 7/2005 | Yang |
| 2005/0232434 | A1 | 10/2005 | Andersen |
| 2005/0288584 | A1 | 12/2005 | McMorrow et al. |
| 2006/0030782 | A1 | 2/2006 | Shennib |
| 2006/0149331 | A1 | 7/2006 | Mann et al. |
| 2006/0241464 | A1 | 10/2006 | Ohtake et al. |
| 2006/0264767 | A1 | 11/2006 | Shennib |
| 2006/0265253 | A1 | 11/2006 | Rao et al. |
| 2007/0106751 | A1 | 5/2007 | Moore |
| 2007/0167801 | A1 | 7/2007 | Webler et al. |
| 2007/0260285 | A1 | 11/2007 | Libbus et al. |
| 2007/0261493 | A1 | 11/2007 | Kim |
| 2007/0276251 | A1 | 11/2007 | Orenstein et al. |
| 2007/0276270 | A1 | 11/2007 | Tran |
| 2008/0004904 | A1 | 1/2008 | Tran |
| 2008/0013747 | A1 | 1/2008 | Tran |
| 2008/0103393 | A1 | 5/2008 | Specht |
| 2008/0319275 | A1 | 12/2008 | Chiu et al. |
| 2010/0036253 | A1 | 2/2010 | Vezina |
| 2011/0270089 | A1 | 11/2011 | Vezina |
| 2013/0102899 | A1 | 4/2013 | Vezina |
| 2013/0102900 | A1 | 4/2013 | Vezina |

OTHER PUBLICATIONS

Anderson G. Chronic Conditions: Making the Case for Ongoing Care. Johns Hopkins University, Baltimore, MD. Nov. 2007, 77 pages.

Jencks et al. Rehospitalizations among patients in the Medicare fee-for-service program. N Engl J Med 2009;360:1418-28.

U.S. Appl. No. 29/457,201, filed Jun. 7, 2013, Vezina.

U.S. Appl. No. 29/457,200, filed Jun. 7, 2013, Vezina.

U.S. Appl. No. 29/457,196, filed Jun. 7, 2013, Vezina.

U.S. Appl. No. 13/912,763, filed Jun. 7, 2013, Vezina.

U.S. Appl. No. 13/179,748, filed Jul. 11, 2011, Vezina.

International Search Report and Written Opinion, PCT/US2009/069474, 10 pages, Feb. 25, 2010.

Hammill BG, Curtis LH, and Bennett-Guerrero E., et al. Impact of heart failure on patients undergoing major noncardiac surgery. Anesthesiology, 2008; 108:559-567.

Pelletier AJ, Ellinor PT, Camargojr CA. Increasing US Emergency Department Visit Rates and Subsequent Hosptial Admissions for Atrial Fibrillation from 1993 to 2004. Ann Emerg Med. Jan. 2008;51(1):58-65.

Eagle KA, Berger PB, and Calkins H, et al. ACC/AHA Guideline Update for Perioperative Cardiovascular Evaluation for Noncardiac Surgery—Executive Summary. A report of the American College of Cardiology/American Heart Associatio Task Force on Pratice Guidelines (Committe to Update the 1996 Guidelines on Perioperative Cardiovascular Evaluation for Noncardiac Surgery). *Anesth Analg.* May 2002;.94(5): 1052-64.

Devereux RB, Roman MJ, Paranicas M, Lee ET, Welty TK, Fabsitz RR, Robbins D, Rhoades ER, Rodeheffer RJ, Cowan LD, Howard BV. A population-based assessment of left ventricular systolic dysfunction in middle-aged and older adults; the Strong Heart Study. Am Heart J. Mar. 2001; 141(3): 439-46.

Devereux RB, Roman MJ, Liu JE, Welty TK, Lee ET, Rodeheffer R, Fabsitz RR, Howard B. Congestive heart failure despite normal ventricular systolic function in a population-based sample: the Strong Heart Study. Am J. Cardiol. Nov. 15, 2000; 86(10): 1090-6.

Maurer MD, Burkhoff D, Fried LP, Gottdiener J, King DL, Kitzman DW. Ventricular structure and function in hypertensive participants with heart failure and a normal ejection fraction; the Cardiovascular Health Study. J Am Coll Cardiol. Mar. 6, 2007; 49(9): 982-85.

Garrett N, Martini EM. The boomers are coming: a total cost of care model of the impact of population aging on the cost of chronic conditions in the United States. Dis Manag. Apr. 2007; 10(2): 51-60.

U.S. Census Bureau. U.S. Interim Projections by Age, Sex, Race, and Hispanic Origin. Http://www.census.gov/ipc/www/usinterimproj/ Mar. 18, 2004. Last accessed Mar. 12, 2008.

Owings MF, Kozak LJ, Ambulatory and inpatient procedures in the United States, 1996. National Center for Health Statistics. Vital Health Stat 13(139), 1998.

Redfield MM, Jacobsen SJ, Burnett JC Jr, Mahoney DW, Bailey KR, Rodeheffer RJ. Burden of systolic and diastolic ventricular dysfunction in the community: appreciating the scope of the heart failure epidemic, JAMA. 2003; 289: 194-202.

Practice Guidelines for Transesophageal Echocardiology. A report by the American Society of Anesthesiologists and the Society of Cardiovascular Anesthesiologists Task Force on Transesophageal Echocardiology. Anesthesiology. 1996:986-1006.

Standards for Basic Anesthetic Monitoring (Approved by the ASA House of Delegates on Oct. 21, 1986, and last amended on Oct. 25, 2005). Http://www.asahq.org/publicationsAndServices/standards/02.pdf last accessed Mar. 12, 2008.

Polanczyk CA, Rohde LE, Goldman L, Cook EF, Thomas EJ, Marcantonio ER, Mangione CM, Lee TH: Right heart catherization and the cardiac complications in patients undergoing noncardiac surgery: An observational study. JAMA 2001; 286:309-314.

Non-Final Office Action, U.S. Appl. No. 12/536,247, mailed Feb. 16, 2012, 24 pages.

Response to Non-Final Office Action, U.S. Appl. No. 12/536,247, filed Jun. 15, 2012; 12 pages.

Notice of Allowance, U.S. Appl. No. 12/536,247, mailed Sep. 18, 2012, 8 pages.

Non-Final Office Action, U.S. Appl. No. 13/179,748, dated Aug. 8, 2014.

* cited by examiner

PERIPHERAL ULTRASOUND DEVICE PROVIDING PIVOTAL ADJUSTMENT OF AN IMAGING MECHANISM ABOUT TWO AXES

CROSS-REFERENCE TO RELATED APPLICATION

The present application is a continuation-in-part patent application of U.S. patent application Ser. No. 12/536,247, filed Aug. 5, 2009, now U.S. Pat. No. 8,348,847 dated Jan. 8, 2013, and titled "System and Method for Managing a Patient;" which claims the benefit under U.S.C. §119(e) to U.S. Provisional Patent Application No. 61/086,254, filed Aug. 5, 2008 and titled "System, Apparatus and Method to Guide Clinical Hemodynamic Management of Patients Requiring Anesthetic Care, Perioperative Care and Critical Care Using Ultrasound." The present application also claims the benefit under 35 U.S.C. §119(e) to U.S. Provisional Patent Application No. 61/140,767, filed Dec. 24, 2008 and titled "Peripheral Ultrasound System for Automated and Uninterrupted Data Acquisition" and U.S. Provisional Patent Application No. 61/224,621, filed Jul. 10, 2009 and titled "System (Apparatus and Method) to Guide Clinical Hemodynamic Management of Patients Requiring Anesthetic Care, Perioperative Care and Critical Care Using Cardiac Ultrasound." The contents of each of the above mentioned applications are hereby incorporated by reference herein in their entireties.

TECHNICAL FIELD

The present disclosure relates to acquiring circulatory system information from a patient. More particularly, the present disclosure relates to acquiring cardiac data points reflecting the function of the heart. Still more particularly, the present disclosure relates to a device and a method for automatically and uninterruptedly acquiring cardiac ultrasound-generated data points allowing a health care provider to optimize the hemodynamic and fluid management of patients.

BACKGROUND

Proper circulatory function is essential to sustain and prolong life. From a more practical standpoint, circulatory function can be a factor affecting health care costs resulting from length of stay in the hospital, complications, hospital readmissions, and mortality. According to some professionals, ensuring the adequacy of circulatory function is one of the most important clinical goals of healthcare providers for anesthetic, perioperative, or critical care procedures. Currently, the American Society of Anesthesiology (ASA) endorses the use of the EKG monitor, systemic blood pressure (BP), pulse oximeter, and urine output (UO), known as the conventional parameters, as the basic standard of care for assessing circulatory function. However, these conventional parameters may not always provide suitable information for managing circulatory function.

Using conventional parameters may be clinically acceptable for patients with normal cardiovascular function. However, conventional parameters often provide incomplete information for patients with cardiovascular risk factors and/or comorbidities. For example, in surgical and critical care settings, managing the circulatory function of a congestive heart failure (CHF) patient with conventional parameters can lead a practitioner to deliver inappropriate amounts of intravenous (IV) fluid and/or maintain an inappropriate level of blood pressure leading to volume overload of the circulatory system of the patient. As a result of the incomplete information, many patients currently undergoing surgical procedures and/or requiring critical care medicine may not receive optimal hemodynamic management. This can lead to cardiovascular complications like acute episodes of CHF, atrial arrhythmias, length of stay in the hospital, hospital readmission after discharge, and even mortality. This result is both detrimental to the health of the patient and costly to the health care system.

This weakness in the standard of care is exacerbated by the fact that CHF, with normal (diastolic dysfunction) or reduced (systolic dysfunction) contractile function, is the leading admission diagnosis for medicine and cardiology services in the United States. Further adding to the problem is that diastolic dysfunction, often the underlying cause of CHF, is common among the baby boomer population. For individuals over 65, 53.8% suffer from some degree of diastolic dysfunction. (40.7% mild and 13.1% moderate or severe). The number of individuals over 65 has been projected to increase by 50% from 2000 to 2020 and as a result, the baby boomer population is recognized as a driving force for healthcare services.

Conventional circulatory function parameters may provide incomplete information for patients with cardiovascular risk factors and/or comorbidities. CHF is an example of one of those conditions and is also a common condition among the baby boomer population and the population as a whole. The health related and economic costs associated with complications, readmissions, and mortality rates need to be addressed. Accordingly, there is a need for a more capable system for managing the hemodynamics of patients.

SUMMARY

In one embodiment, a device for acquiring ultrasound-generated data from a patient can include a securing system and a probe configured for connection to the securing system. The probe can include a base having an interfacing surface. The probe can also include an imaging mechanism adjustable relative to the base and configured to send and receive ultrasound signals along an imaging direction. The probe can also include an adjustment mechanism configured to adjust the imaging mechanism relative to the base thereby adjusting the imaging direction. The adjustment mechanism can include a first adjustment mechanism configured to adjust the imaging mechanism about a first axis generally orthogonal to the interfacing surface, the first adjustment mechanism comprising an annular ring oriented parallel to and offset from the interfacing surface and having a an orientation actuator operably coupled thereto for pivoting the imaging mechanism about the first axis. The adjustment mechanism can also include a second adjustment mechanism configured to adjust the imaging mechanism about a second axis generally parallel to the interfacing surface, the second adjustment mechanism comprising a gear extending from the imaging mechanism and being positioned generally orthogonal to the interfacing surface and having a direction actuator operably coupled thereto for pivoting the imaging mechanism about the second axis.

In another embodiment, a probe for acquiring ultrasound-generated data can include a housing having an interfacing surface with an opening and an imaging mechanism positioned in the opening. The imaging mechanism can be rotatable in a plane generally parallel to the interfacing surface and pivotal about an axis generally orthogonal to the interfacing surface. The probe can also include an adjustment mechanism positioned within the housing and associated with the imaging mechanism to cause the imaging mechanism to rotate in the plane or pivot about the axis, the adjustment mechanism comprising an orientation adjuster and a direction adjuster each having an orientation actuator and a direction actuator respectively.

In another embodiment, a securing system for securing a probe to a patient can include an anchoring member, an adhesive feature positioned on the anchoring member, and a retention member connected to the anchoring member and configured to secure a probe thereto. In some embodiments, the securing system can include a probe recognition module arranged on a portion of the anchoring member or the retention member and can include a bar code or an electronic circuit. In other embodiments, the probe recognition module can include a chip embedded in the anchoring member and configured to perform a calibration protocol.

BRIEF DESCRIPTION OF THE FIGURES

While the specification concludes with claims particularly pointing out and distinctly claiming the subject matter that is regarded as forming the various embodiments of the present disclosure, it is believed that the embodiments will be better understood from the following description taken in conjunction with the accompanying Figures.

DETAILED DESCRIPTION

The present disclosure relates to devices and methods for acquiring ultra-generated data points from a patient. In particular, the present disclosure includes discussion of a device including an ultrasound probe and a securing system. In contrast to handheld devices, the securing system can allow for securely positioning a probe on a patient allowing for hands-free capture of ultrasound images. The ultrasound image captured can be manually or automatically adjusted by manual or automatic manipulation of a transducer of the probe such that uninterrupted data acquisition can be performed. The device can be used to acquire cardiac ultrasound-generated data, particularly relating to blood flow inside and in structures connected to the heart.

The device can be used, for example, with the System for Managing a Patient described in patent application Ser. No. 12/536,247 referenced above. In some embodiments, the device can be used with a computer, such as a laptop computer, a desktop computer, and the like. In either case, one device can be used or multiple devices can be used to facilitate efficient acquisition of ultrasound-generated data by placing the devices at multiple vantage points on a patient.

Figure 1:
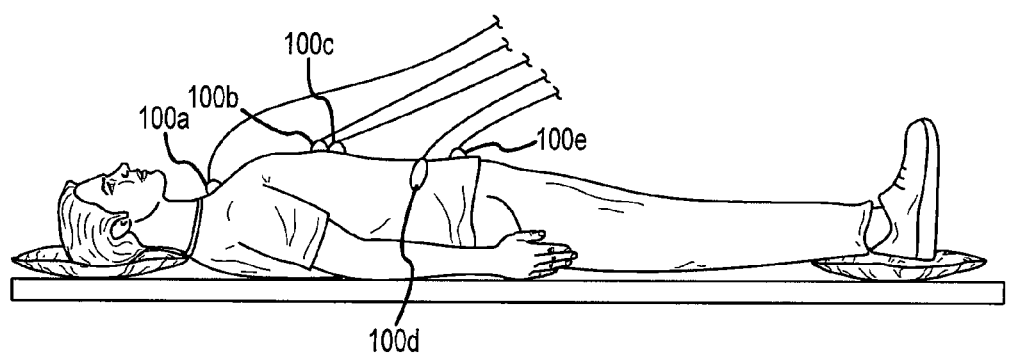
FIG. 1 shows a patient having a plurality of devices positioned on the patient in locations conducive to collection of cardiac ultrasound-generated data points.

Referring to FIG. 1, a patient is shown with five devices 100a-e in position on the generally anterior surface of the body. In the embodiment shown, for example, the devices 100a-e can be placed in cardiac viewing windows such as the transthoracic parasternal window, the transthoracic apical window, the sub-costal window, and the suprasternal notch window. Additional devices 100 can be used to image more superficial and/or non-cardiac structures.

Figure 2:
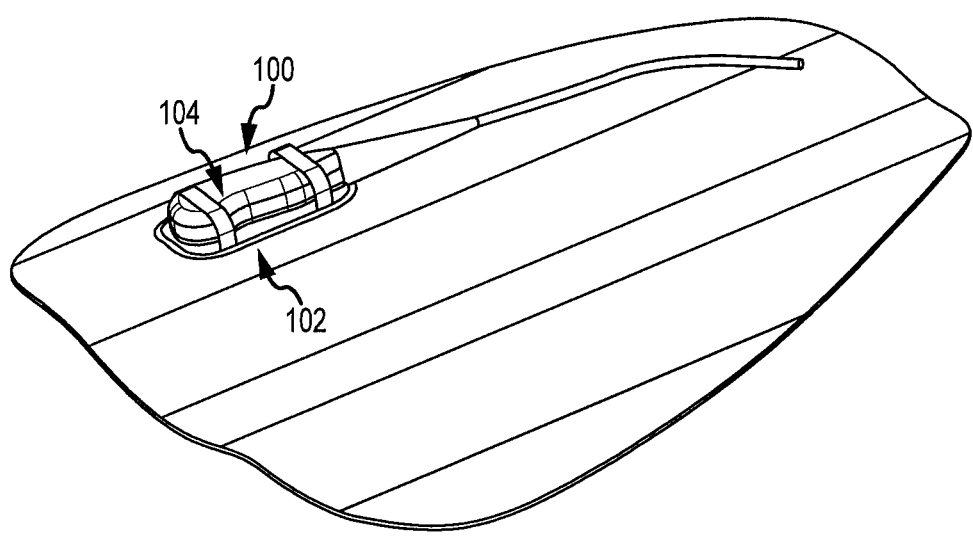
FIG. 2 shows a close-up view of one of the devices of FIG. 1 in position on the patient.

Referring now to FIG. 2, a close-up view of one of the devices 100 of FIG. 1 is shown. As shown, the device can include a securing system 102 and a probe 104. The securing system 102 can be positioned on the patient and can be adapted to adhere or otherwise anchor itself to the surface of the patient. The securing system 102 can further be configured to receive the probe 104 and connect to the probe 104 thereby securing the probe 104 to the location on the patient at which the securing system 102 is secured. It is noted that in some embodiments, a securing system 102 may not be provided and the probe 104 may be directly positioned on the patient.

Each of the securing system 102 and the probe 104 will now be described in detail. The probe 104 can be initially described with reference to FIGS. 3-6 and the securing system 102 can be described with respect to FIGS. 10 and 11. However, it is to be understood that concepts are presented that are generic to some or all of the embodiments described in the specification and as such are not limited to the embodiments in the particular figures referenced.

Beginning first with the probe 104, the probe 104 can be adapted for connecting to the securing system 102 and can be configured to send and receive ultrasound signals to capture ultrasound-generated data from a patient. The probe 104 can further be configured for adjustability to allow the signals to be sent and received in a suitable orientation and direction relative to the probe 104 position on the patient. Accordingly, the probe 104 can include a base structure for connecting to the securing system 102, an imaging mechanism for sending and receiving ultrasound signals, and an adjustment mechanism for adjusting the orientation and/or direction of the imaging mechanism. In some embodiments, the probe 104 may also include a control module in the form of hardware, software, or a combination thereof for controlling all or a portion of the imaging and/or adjustment mechanism.

The base structure of the probe 104 can include a broad range of items. The base can be configured to connect to the securing system 102 and further support the imaging mechanism. To this end, the base structure can include a housing, a frame, a platform, a cage, a plate, a plurality of legs, or some combination of these elements, for example. Other base structures can be used. The base structure can be configured to interact with the securing system 102 through interactive features such as, for example, physical connections, electrical communications, data communications, or other interactive features. The base can thus include surfaces, ports, connection elements, electrical and/or communicative contacts, or communicative surface images or textures. Other interactive features can be provided.

Figure 3:
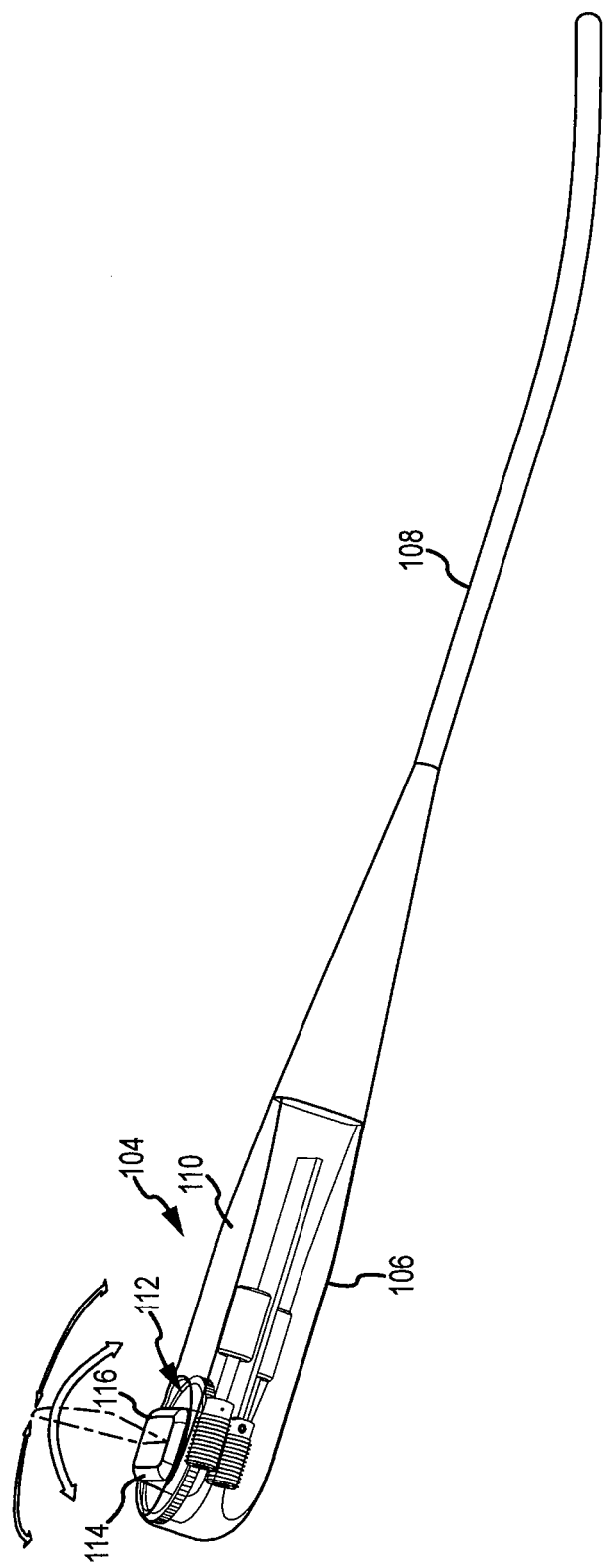
FIG. 3 shows a perspective view of a probe of one of the devices of FIGS. 1 and 2, according to certain embodiments.

Referring now to FIG. 3, in the embodiment shown, the base structure is in the form of a housing 106. The housing 106 can be any shape including rectangular, square, round, elliptical or any shape. In the embodiment shown, the housing 106 has a generally rectangular cross-section with radiused corners. At the distal end of the housing 106, the lateral sides of the rectangular cross-section follow an arcuate path and intersect with one another to form an arcuate distal end wall. At the proximal end of the housing 106, the lateral sides taper inward to narrow the cross-section of the housing 106. The proximal end of the housing 106 can be adapted for connection to a lead 108.

The housing 106 can be configured to support an imaging mechanism and as such can be a generally hollow structure. The housing 106 can include shoulders, ledges, cavities, tabs, plates, or other internal features adapted for connection of internal components or parts. As shown, the housing 106 can include an interactive feature in the form of an interfacing surface 110. The interfacing surface 110 can be adapted for placement against the securing system 102 and/or directed toward the patient. The interfacing surface 110 of the probe 104 can include an opening 112 for exposing the imaging mechanism. The opening 112 can be any shape. In the embodiment shown, the opening 112 is a round opening and is thus adapted to accommodate rotational adjustment of the orientation of the imaging mechanism positioned therein.

Turning now to the imaging mechanism, this element of the probe 104 can be configured to send and receive ultrasound signals. Accordingly, the imaging mechanism can be in the form of an ultrasound transducer 114. Other imaging mechanisms can be included for other purposes such as X-ray, CT scan, MRI, or other image generating mechanisms.

The ultrasound transducer 114 can be adapted for obtaining information suitable for two-dimensional imaging, three-dimensional imaging, B-mode, M-mode, color Doppler, and spectral Doppler output. The transducer 114 can be built with piezo-electric crystals adapted to emit ultrasonic signals. The transducer 114 can include a suitable crystal array. For example, the transducer 114 can be constructed with a phased array of crystals, a matrix of a phased array of crystals, or a convex linear array. The phased array of crystals may provide for a two dimensional pie-shaped cross-sectional image. The matrix may provide for a three dimensional image. The probe 104s adapted to image more superficial elements can include transducers 114 constructed with a linear array of crystals allowing for higher frequency imaging and may provide for a rectangular image. The arrays can contain a small number of elements (in the hundreds) up to a large number of elements (in the thousands). The elements may be configured to generate one or more two-dimensional images at the same time, three-dimensional images or real-time three-dimensional images also called four-dimensional images. The configuration of elements may be a matrix or a mesh-like design of elements allowing volume rendering of the imaged structures. Other arrangements of crystals such as, for example, a circular array can be used and are within the scope of the disclosure. Moreover, mechanical transducers could be used in lieu of or in addition to the piezo-electric crystal type transducers described.

The transducer 114 can have a signal emitting surface 116 adapted for interaction with the patient. As such, the signal emitting surface 116 can be generally flat or contoured to suitably engage the surface of a patient. The signal emitting surface 116 can be rectangular, square, or round. Other shapes can be provided.

The transducer 114 can be mounted within the housing 106 such that it can rotate about an axis generally orthogonal to the interfacing surface 110 of the housing 106. Additionally or alternatively, the transducer 114 can be mounted within the housing 106 such that it can pivot about an axis generally parallel to the interfacing surface 110. It is noted here that the transducer 114 can be mounted directly to the housing 106 where the mounting allows for the rotation and/or pivoting described. In this embodiment, the adjustment mechanism described below can act on the transducer 114 to adjust its orientation and/or direction. Alternatively, the transducer 114 can be mounted to the housing 106 by way of the adjustment mechanism. The transducer 114 can be positioned relative to the housing 106 in a position to interact with the surface of a patient. In some embodiments this may include projecting beyond the interfacing surface 110 an amount approximately equal to the thickness of the securing system 102. As will be described and shown with respect to FIGS. 10 and 11, the securing system 102 may include an opening 118 through which the ultrasonic signals are directed and as such, the transducer 114 may project into this opening 118 when connected thereto. In other embodiments, the transducer 114 may be mounted more flush with the interfacing surface 110 or even recessed relative thereto.

Figure 4:
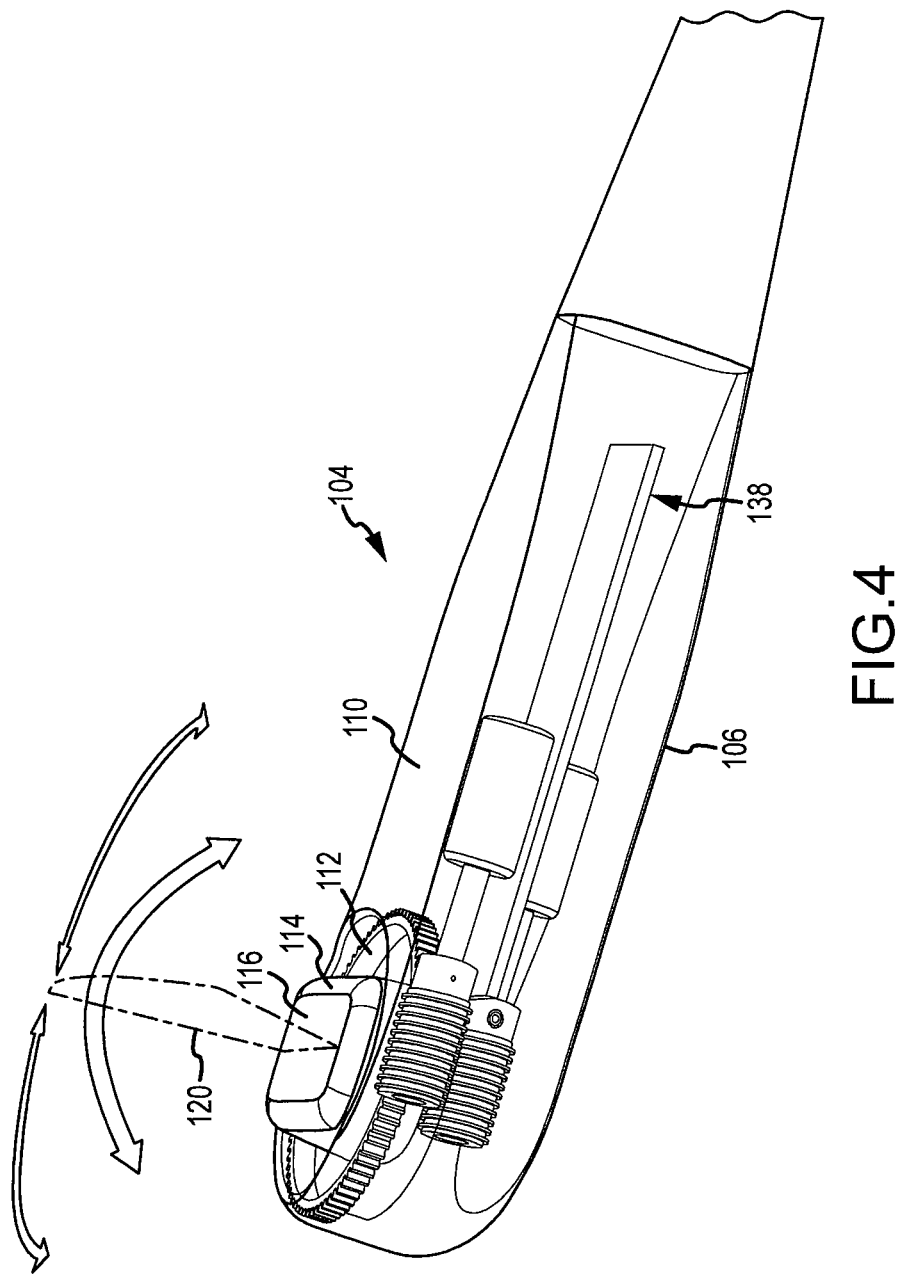
FIG. 4 shows a close-up perspective view thereof.

Referring particularly to FIG. 4, in the embodiment shown, the imaging mechanism is in the form of a transducer 114 constructed with a phased array of crystals as depicted by the pie shaped cross-section image 120 emanating from the signal emitting surface 116. The signal emitting surface 116 is shown as a generally flat rectangular surface and the transducer 114 is shown to project slightly beyond the interfacing surface 110 of the housing 106. In the present embodiment, the transducer 114 is shown mounted to the housing 106 by way of the adjustment mechanism to be described next.

Turning now to the adjustment mechanism, this element of the probe 104 can be configured to adjust the orientation and/or direction of the imaging mechanism. For purposes of discussion, it should be understood that the orientation relates to the rotational orientation of the imaging mechanism in a plane parallel to the interfacing surface 110 of the housing 106 and the direction relates to a centerline of the profile of the cross-sectional image 120. As such, for a pie-shaped cross-section, for example, the direction of the imaging mechanism, can be defined by a line bisecting the pie-shaped profile and in the plane of the pie-shaped profile. The adjustment mechanism may be configured to rotate the imaging mechanism about a line extending generally orthogonal to the interfacing surface 110. As such, the adjustment mechanism can include an orientation adjusting mechanism. Alternatively or additionally, the adjustment mechanism may be configured to pivot the imaging mechanism about an axis extending generally parallel to the interfacing surface 110. As such, the adjustment mechanism may further include a direction adjusting mechanism.

The adjustment mechanism can include one or more actuation mechanisms for inducing the adjustment of the imaging mechanism. The actuation mechanisms can range between manual and automatic mechanisms and combinations thereof can also be provided. In the case of manual mechanisms, theses may include thumb screws, lever arms, graspable rotating or sliding knobs, or accessible pivot or translational shafts. Other manual adjustment mechanisms can be provided. In the case of automatic adjustment mechanisms, these may include piston type actuators, screw gear type actuators, rotating gear type actuators, or compressed air systems. Other automatic mechanisms can be provided. Regarding combinations of manual and automatic mechanisms, in some embodiments, the mechanisms listed above as automatic mechanisms may be manually adjusted via input received into a controller of the automatic mechanism.

These manual and automatic mechanisms may allow for adjustment of the orientation and/or direction of the image mechanism to more suitably capture the ultrasonic data. In some embodiments, the manual adjustment may be used to position the image mechanism in the approximate orientation and direction and the automatic mechanism may then refine the adjustment. It is noted that, while the term manual has been described as adjustments that are made by hand and automatic has been described as adjustments made with mechanical or electromechanical devices, the term manual can also include relying on a user interface to manually enter a orientation and/or direction causing the actuating device to adjust the image mechanism accordingly.

As mentioned above, this adjustment of the imaging mechanism may include manipulating the imaging mechanism about its supports on the base structure or the imaging mechanism may be supported by the adjustment mechanism and the adjusting may occur through adjustment of a portion of the adjustment mechanism. In the case of an adjustment mechanism isolated from the support of the imaging mechanism, the adjustment mechanism can include one or more actuators configured to cause the imaging mechanism to move about its support to the housing. For example, where the imaging mechanism is supported by the base via a pivot pin, the adjustment mechanism can include a longitudinally telescoping actuator that presses or pulls on a side of the imaging mechanism offset from the pivot axis thereby causing the imaging mechanism to pivot about the pivot pin. In the case of an adjustment mechanism integral with the support of the imaging mechanism, the adjustment mechanism can include one or more actuators configured to cause a portion of the adjustment mechanism to move and carry the imaging mechanism therewith. For example, where the imaging mechanism is supported on a rotating portion of the adjustment mechanism, an actuator may cause the rotating portion to rotate causing the imaging mechanism to rotate also. In other embodiments portions of the actuation mechanism can move with the imaging mechanism, while other portions remain stationary relative to the base structure.

Figure 5:
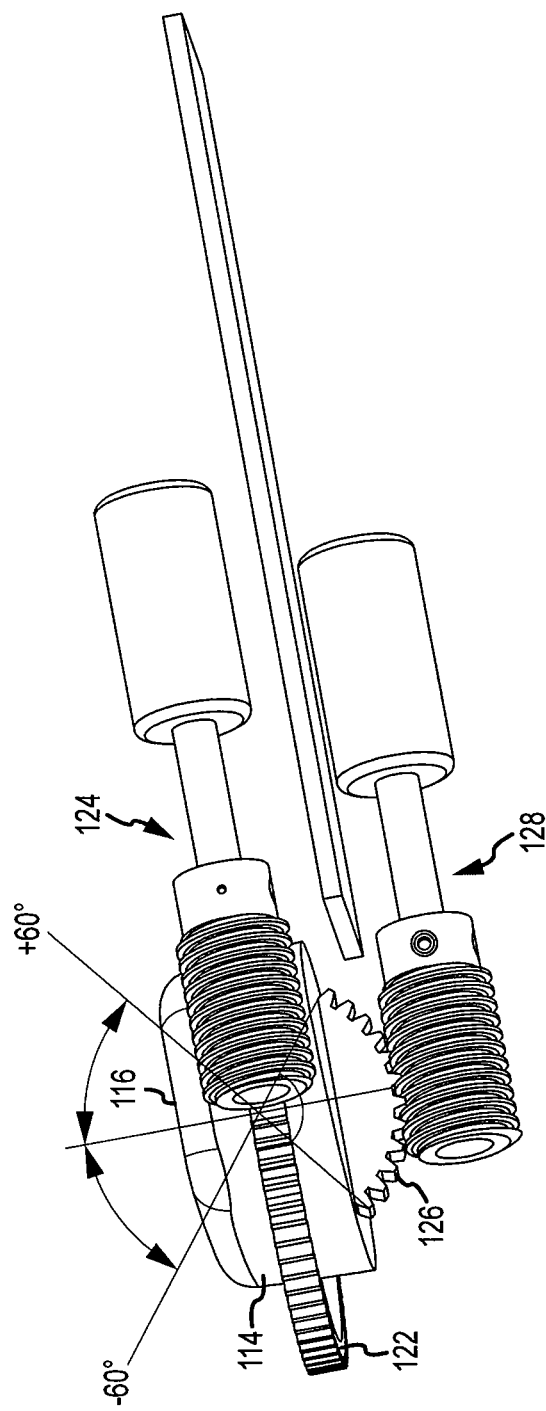
FIG. 5 shows a partial perspective view of the probe of FIGS. 3 and 4.

Referring now to FIG. 5, in the embodiment shown, the adjustment mechanism is configured to rotate the transducer 114 about an axis extending generally orthogonal to the interfacing surface 110 and is further configured to pivot the transducer 114 about an axis extending generally parallel to the interfacing surface 110. In this embodiment, the orientation adjusting mechanism can include an orientation guide 122 and an orientation actuator 124. The direction adjusting mechanism can include a direction guide 126 and a direction actuator 128.

The orientation guide 122 can be in the form of an annular ring positioned in the housing 106 to rotate about an axis extending generally orthogonal to the interfacing surface 110. In this embodiment, the housing 106 may include a generally annularly extending channel. The channel can extend around an inside surface defined by the shape of the opening 112 in the housing 106 and the annular ring can be slidably positioned therein. The annular ring can include a plurality of gear teeth on an outer periphery thereof forming a rack engageable by the orientation actuator 124.

The orientation actuator 124, in this embodiment, can include a stationary screw driven by a rotating motor. The stationary screw can be positioned in a cavity within the housing 106 such that it can slidably rotate in the cavity without translating. Alternatively or additionally, the stationary screw can be supported by a shaft extending from the motor. The motor can be mounted within the housing 106 in a cavity or via brackets, mounting locations, or other techniques. The annularly extending channel containing the annular ring can include an opening allowing access to the annular ring by the orientation actuator 124. The stationary screw can be positioned tangentially along the periphery of the annular ring such that threads of the stationary screw extend through the opening in the channel and engage the teeth on the outer periphery of the annular ring. As such, actuation of the rotating motor can rotate the stationary screw causing the annular ring to rotate relative to the housing 106. The device shown can allow for a full 360° rotation of the annular ring.

In this embodiment, the stationary screw shown is positioned generally longitudinally with respect to the housing 106. However, it will be appreciated that the screw can be reoriented with respect to the housing 106 and can function similarly at any tangential orientation to the annular ring.

Figure 6:
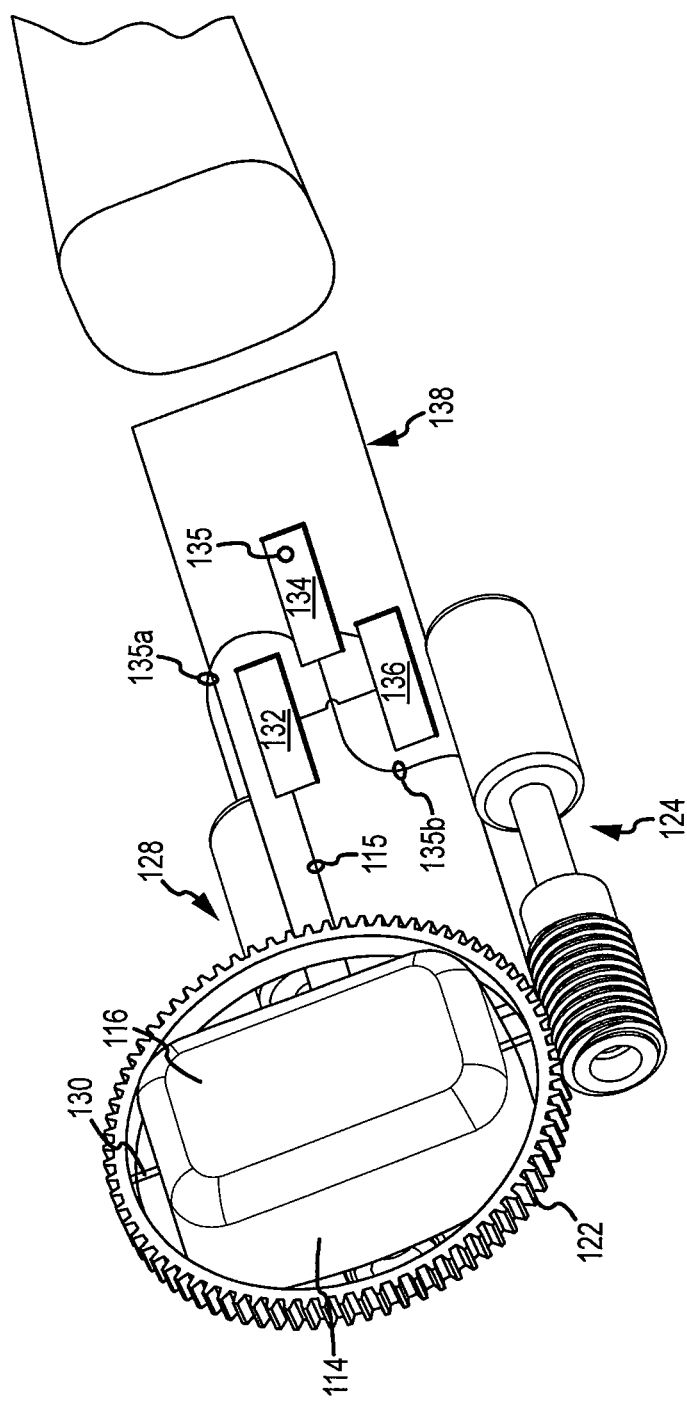
FIG. 6 shows another partial perspective view of the probe of FIGS. 3 and 4.

As best shown in FIG. 6, the transducer 114 of this embodiment can be pivotally supported within the annular ring by, for example, a pivot pin 130 extending across the annular ring. Due to the connection to the annular ring, the actuation of the rotating motor of the orientation actuator 124 can, thus, cause rotation of the transducer 114.

The direction guide 126 can be in the form of a gear. In the embodiment shown, the gear is a semicircular gear and is positioned to extend from the transducer 114 in a plane generally orthogonal to the interfacing surface 110 and further generally orthogonal to the pivot pin 130 supporting the transducer 114. The semicircular gear can be positioned on the transducer 114 such that the center point of the gear is located at the pivot axis or pivot pin 130 of the transducer 114. The semicircular gear can include teeth extending along the periphery of the semicircular shape forming a rack.

The direction actuator 128, in this embodiment, can also include a stationary screw driven by a rotating motor. The stationary screw can be the same as that described with respect to the orientation actuator 128 and can be supported in the same or similar fashion. The stationary screw of the direction actuator can be positioned tangentially along the periphery of the semicircular gear such that the threads of the screw engage the teeth on the gear causing the periphery of the gear to translate along the arc defined by the radius of the gear. The connection of the gear to the transducer 114 and the corresponding center point of the gear with the pivot point of the transducer 114 can allow the transducer 114 to pivot thereby adjusting the direction of the transducer 114. The direction of the transducer 114 can thus be adjusted from approximately −60° to approximately +60° as shown in FIG. 5. The range of direction of the transducer 114 can be larger or smaller depending on the arc length of the semicircular gear and any adjustment range can be provided. It is noted that the nature of ultrasound transducers 114 causes them to function best when the signals do not travel through materials with changing densities. As such, in some embodiments, the adjustment range of the transducer 114 may be limited to angles allowing the signal emitting surface 116 to maintain contact with the body surface, the securing system 102, or an ultrasonic gel.

Additionally, in this embodiment, the stationary screw is shown positioned generally longitudinally with respect to the housing 106. However, it will be appreciated that the screw can be reoriented with respect to the housing 106 and can function similarly at any tangential orientation to the gear. It is further noted that the gear, while shown to extend rearward from the transducer 114 can extend from the sides of the transducer 114 or a gear encompassing a larger included angle can be provided such that the gear extends along the rearward face and sides of the transducer 114.

In the embodiment shown, it can be appreciated that orientation adjustments of the imaging mechanism can cause the gear to rotate out of alignment with the screw of the direction actuator 128. Accordingly, in this embodiment, the threads on the screw and the gear teeth on the gear may include a degree of play allowing the change in orientation of the gear without a loss of function.

Figure 24:
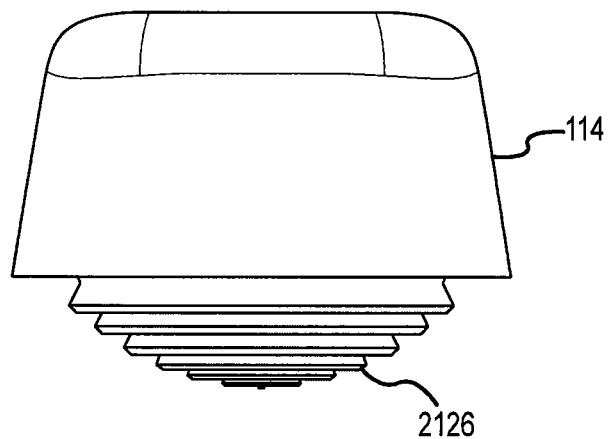
FIG. 24 shows an embodiment of a direction guide according to certain embodiments.
Figure 24:
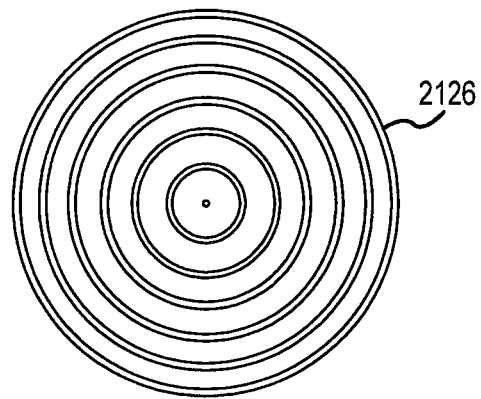

In another embodiment, as shown in FIG. 24, a gear can be provided that allows for the change in orientation between the gear and the direction actuating screw. As shown, the gear can be a ball gear 2126 and the gear teeth can be positioned on the sphere and can pass around the sphere and maintain a radial distance from an axis extending generally perpendicular to the interfacing surface and centered on the annular ring. As such, when the orientation of the imaging mechanism is adjusted, the curved gear teeth on the ball gear will maintain alignment with the screw as the imaging mechanism rotates.

Figure 25:
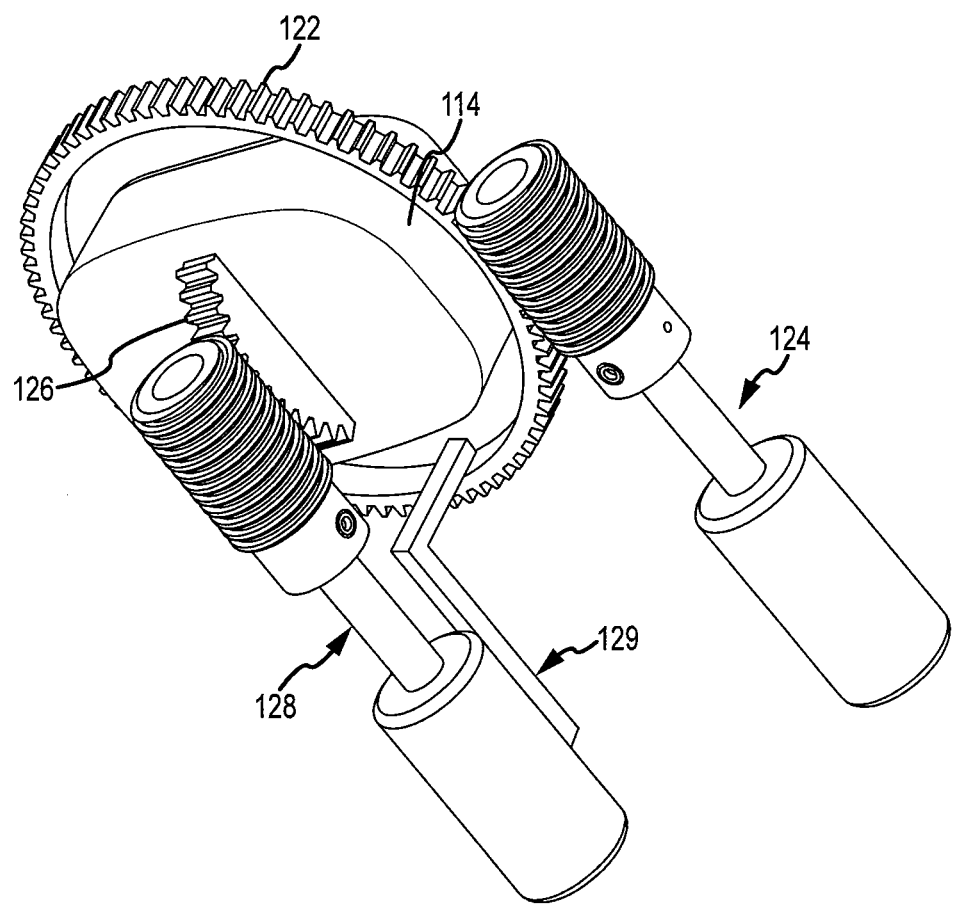
FIG. 25 shows an embodiment of a direction actuator according to certain embodiments.
Figure 26:
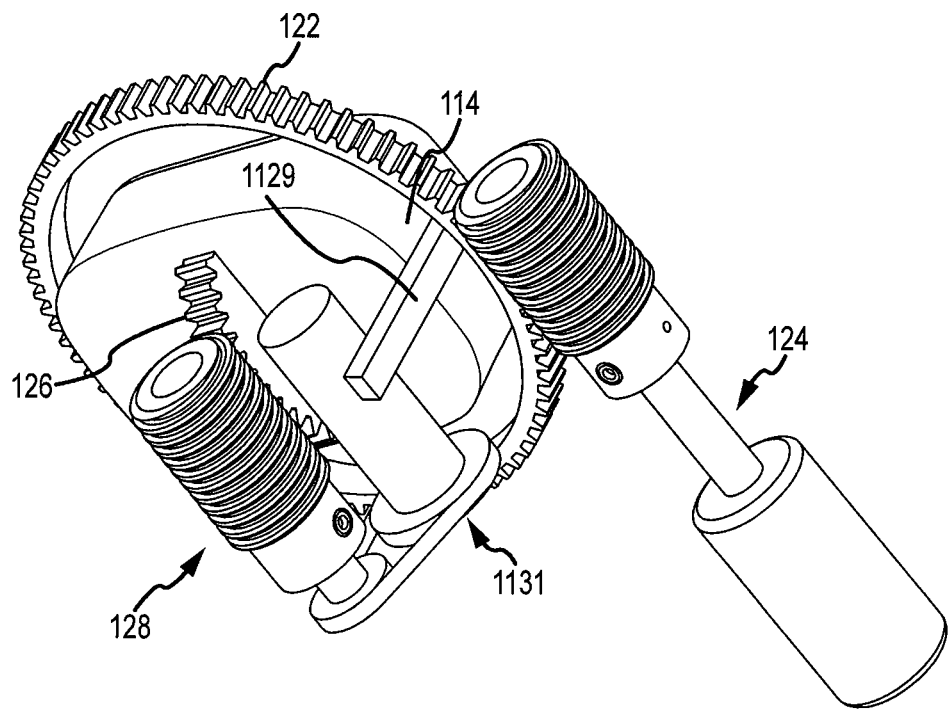
FIG. 26 shows an embodiment of a direction actuator according to certain embodiments.

In still another embodiment, as shown in FIG. 25, the direction actuator 128 can be affixed to the orientation guide 124 such that the direction actuator 128 rotates together with the gear 126 and maintains alignment therewith. As shown in FIG. 25, in one embodiment, the annular ring can include a support 129 in the form of a strut, cage, semispherical surface or other structure extending therefrom for mounting of the direction actuator 128 thereto. As shown, the support can allow for the suspending the direction actuator 128 from the annular ring allowing for pivoting motion of the imaging mechanism relative thereto. In one embodiment, as shown in FIG. 26, the direction actuator can be rearranged such that the motor portion is adjacent to the screw portion rather than in longitudinal connection. A support 1129 similar to that shown in FIG. 25 can be provided to support the motor from the annular ring and geared, belted, or other system 1131 can be provided to transfer rotational motion from the motor to the screw adjacent the motor.

Turning now to the control module 138, and referring still to FIG. 6, this element of the probe 104 can include hardware, software, or a combination thereof for controlling certain aspects of probe 104 and/or system functionality. As such the control module 138 can include some or all of an image mechanism component 132, a adjustment mechanism component 134, and an analysis component 136. Each of these modules or components thereof, can include software or a portion thereof, hardware or a portion thereof, or a combination of software and hardware adapted to perform a process. Each module or component thereof can be combined or overlapped with or combined with modules or components performing other tasks in the process. In some embodiments, this overlap or combination may include tasks or steps adjacent to one another in a process, but in other embodiments, the tasks and steps may not be adjacent one another. Moreover, any module or component thereof may or may not be included in the system depending on the nature of the system desired. Additionally, the control module 138 or any module or component thereof can each include an input and output module adapted to receive or send information from or to, respectively, other devices, modules, or components. As such, these input and output modules can include physical ports or connection to a bus where the input or output module is of the hardware type. Other types of input and output hardware can be used. In the case of software based input and output modules, these can include lines of code causing a processor to step or jump from one location to another or an application programming interface, for example. Other types of software based input and output can also be used.

The image mechanism component 132 can be configured to control, for example, the transducer 114. As such, the image mechanism component 132 can be configured to generate, transmit, and receive ultrasound signals. The generation of ultrasound signals can include beam forming and/or array beam forming. Transmitting and receiving ultrasound signals can include one or more processing functions for emitting ultrasonic signals and capturing the results from the reflected signal. The image mechanism component 132 may include task specific hardware or software and can be in electrical communication with the transducer 114 via lead 115 as shown.

The adjustment mechanism component 134 can be configured to control the adjustment mechanism. As such, the adjustment mechanism component 134 can include hardware and or software that is adapted to activate and deactivate one or more actuators associated with the adjustment mechanism and further control the direction of motion. For example the adjustment mechanism component 134 can be configured to activate the rotating motors of FIG. 6 to turn the stationary screws. The adjustment mechanism component can further be adapted to control the direction of the motors such that the stationary screws can turn in a particular direction and suitably adjust the orientation and/or direction of the image mechanism. The adjustment mechanism component can be in electrical communication with the motors as shown, via leads 135a and 135b as shown.

This component 134 can be in communication with an analysis system such as that described in U.S. patent application Ser. No. 12/536,247 that is capable of analyzing ultrasonic images. As such, the analysis system may trigger the adjustment mechanism component 134 to adjust the orientation or direction of the image mechanism in one direction or another based on the quality of the image being captured. In some embodiments, the initial image may be adjusted by the user via a manual adjustment on the probe 104 or via an input adjustment into the analysis system. As such, the initial calibration of the images may include user interaction or the analysis system may do so by comparing the captured images to standards or desired quality images.

In some embodiments, the adjustment mechanism component 134 may include a gating component 135 configured to adjust the orientation and/or position of the image mechanism to accommodate movement of the patient due to breathing. In some embodiments, this gating component 135 can be in communication with motion sensors adapted to sense the motion of a patient. Based on this motion, the gating component 135 can further provide additional information to the adjustment mechanism component 134 of the control module 138 to cyclically adjust the adjustment mechanism thereby maintaining the scanning plane in a consistent position relative to the structures being viewed by the image mechanism. In another embodiment, the gating component 135 can be adapted to monitor the image appearance and disappearance as the patient breathes thereby being able to develop frequency and period information particular to a given patient's current breathing pattern. The magnitude of adjustment of the adjustment mechanism can be related to the amplitude of the breathing of the patient. As such, the gating component, having determined the frequency of breathing, can gradually increase the magnitude of the adjustment until the scanning plane maintains a substantially constant view of the structure being viewed throughout the breathing cycle. This gating component 135 can thus allow for uninterrupted acquisition of ultrasound-generated data due to the consistency of the image plane relative to the targeted structures as the image mechanism moves together with the patient.

The analysis component 136 can include software and/or hardware adapted to perform any and/or all of the methods and processes described in U.S. patent application Ser. No. 12/536,247 referenced above. For example, the analysis component 136 may include software or hardware configured to analyze the received ultrasound-generated data points and assist a user in managing the hemodynamic status of a patient.

The control module 138 can be provided with one of several different levels of control capability. In some embodiments, the control module 138 can include relatively little control capability. In this embodiment, the control module may include the image mechanism component 132. In another embodiment, the control module 138 may further include the adjustment mechanism component 134 and in still another embodiment, the probe 104 may further include the analysis component 136. Where the control module 138 is provided with less than all of the control related components, these components can be provided by another system in communication with the probe 104.

Figure 7:
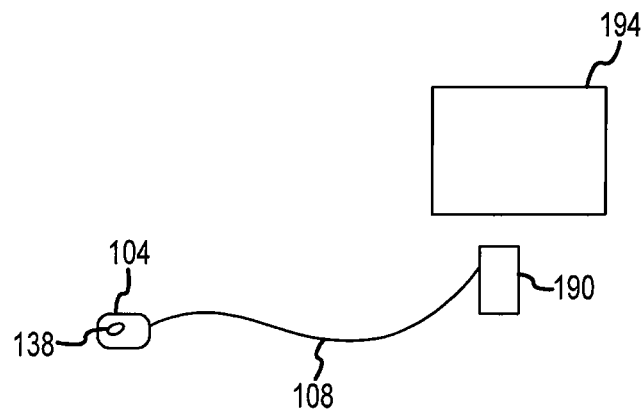
FIG. 7 depicts an exemplary system including a device according to certain embodiments.
Figure 8:
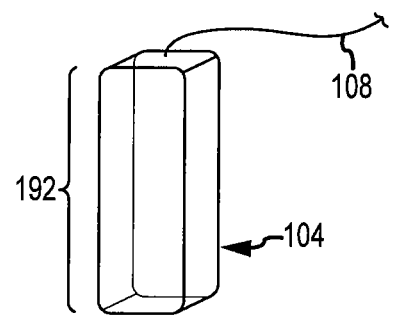
FIG. 8 shows a perspective view of a probe according to certain embodiments.
Figure 9:
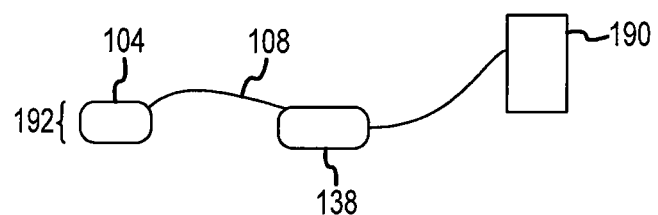
FIG. 9 depicts and exemplary device according to certain embodiments.

The control module 138 can be located within the probe 104 as shown, for example in FIG. 4. In this embodiment, a lead 108 may extend proximally from the probe 104 to a system interface 190 adapted to communicate with a system 194, as shown in FIG. 7. In this embodiment, the probe 104 may have a relatively large profile 192 (e.g., greater than 5 cm) as shown in FIG. 8. In another embodiment, as shown in FIG. 9, the control module 138 can be located relatively remote from the probe 104. In some embodiments, this remote distance can range from a few centimeters to a foot. Positioning the control module 138 remote from the probe 104 may allow the probe 104 to have a reduced profile 192 (e.g., less than 5 cm). It is noted that the size of the probe 104 can also be dependent on the size and orientation of the image mechanism and the adjustment mechanism, where the image mechanism size is further dependent on the type of piezoelectric crystal arrangement being used.

The probe 104 can thus be used with varying levels of support systems depending on the capability of the control module 138. At one end of the spectrum, the probe 104 can be interfaced with a system 194 similar to that described in U.S. patent application Ser. No. 12/536,247. In this embodiment, the probe 104 can have a control module 138 having the image mechanism component 132 and control of the actuation mechanism and analysis can be performed by the attached system 138. Alternatively, the control module 138 can further include a adjustment mechanism component 134 leaving the system to control the analysis. At the other end of the spectrum, where the control module 138 includes each of the image mechanism component 132, the adjustment mechanism component 134, and the analysis component 136, the probe 104 may be capable of use by interfacing the probe 104 with a user interface. In this example, the probe 104 may, for example, be connected to a USB port of a computer and a specialized ultrasound machine may or may not be provided.

Having described one embodiment of the probe 104 in great detail, a securing system 102 will now be described. The securing system 102 can be positioned on the patient and can be adapted to adhere or otherwise anchor itself to the surface of the patient. The securing system 102 can further be configured to receive the probe 104 and connect to the probe 104 thereby securing the probe 104 to the location on the patient at which the securing system 102 is secured. As such, the securing system 102 can include an anchoring member with an adhesive feature, a probe connecting system, and a recognition module.

Regarding the anchoring member, this element may be configured to adhere to the patient. The anchoring member can be a generally planar member so as to provide a pad like location for placement of the probe 104. Alternatively, the anchor member can be a tubular or port type member to provide for insertion of the probe 104 therein. Other shapes and types of anchoring members can be provided for receiving and connecting to the probe 104. The anchoring member can include a patient interface 140 adapted for placement against the skin of a patient. The patient interface can include a relatively flat or slightly contoured surface. The anchoring member can further include an adhesive feature. The adhesive feature can be in the form of a biocompatible adhesive membrane positioned on the patient interface 140 or the adhesive feature can be a tape like feature having a size at least slightly larger than the anchoring member. The tape-like feature can be adapted to cover the anchoring member and secure the member to the patient. The tape-like feature can include perforations to accommodate the probe 104 or the tape-like feature may cover both the probe 104 and the anchoring member. The securing system 102 can also be secured on the patient body surface using an external securing mechanism. The external securing mechanism may be either straps, hooks, loops, elastics, hook and loop bands, belts and or tie-downs attached to the edges to the material and wrapped around the patient's body.

Figure 10:
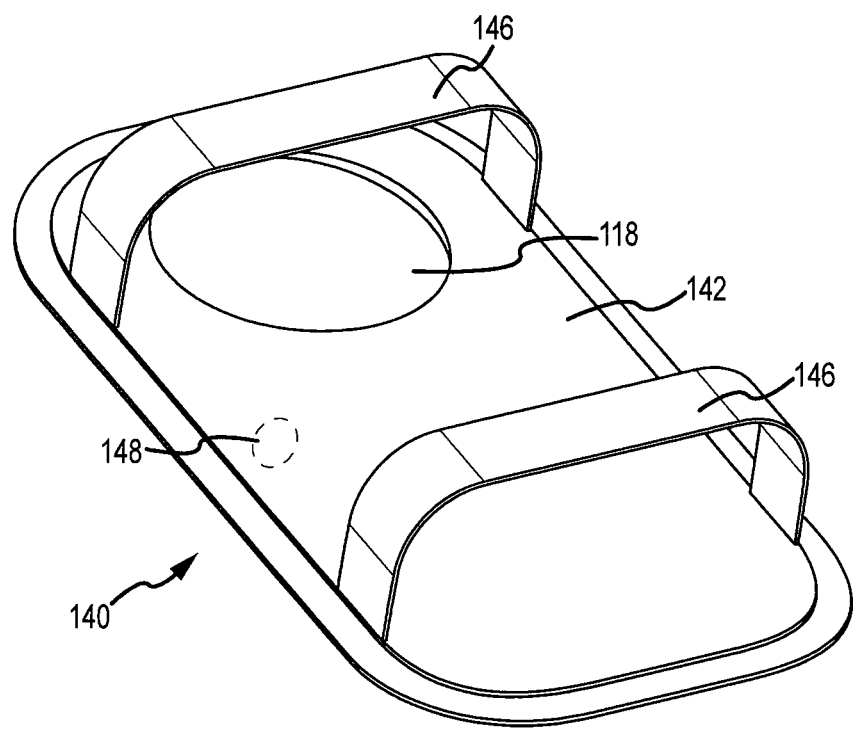
FIG. 10 shows a close-up perspective view of a securing system of the device of FIGS. 1-2.
Figure 11:
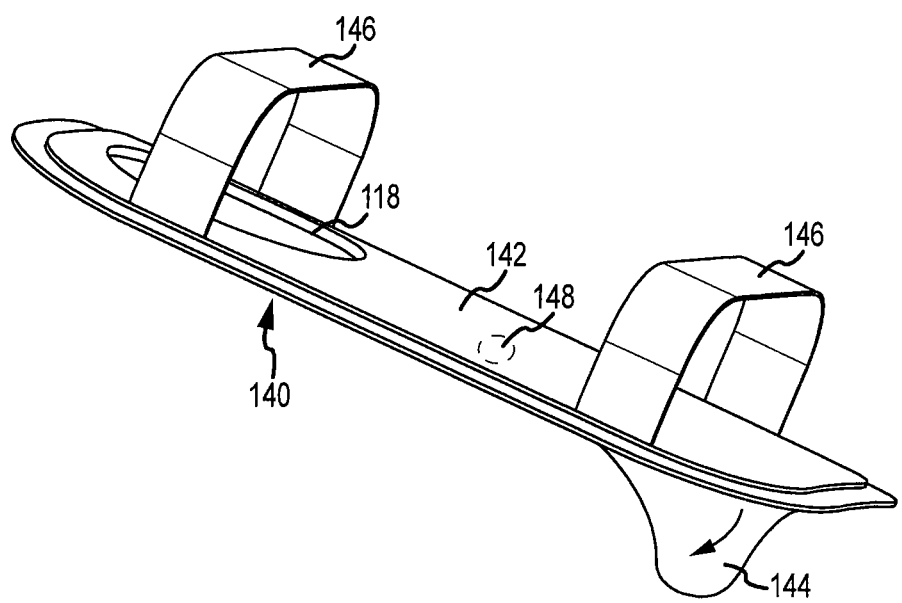
FIG. 11 shows an additional close-up perspective view thereof.

Referring to FIG. 10, the anchoring member shown is in the form of a generally planar patch 142. The patch 142 is generally rectangular, relatively thin, and flexible. The patch 142 may be a multilayer patch a shown in FIG. 11 or a single layer may be provided. The patch 142 may be made from soft flexible materials that may conform to the contours of a patient's skin. As shown, the anchoring member includes a patient interface 140 adapted for contact with the patient. In the embodiment shown, the patient interface 140 can be coated with an adhesive membrane. In some embodiments, the adhesive membrane can be protected prior to use with a protective peel-away membrane 144 in the form of cellophane or other protective membrane fabric.

The securing system 102 may further include a probe connecting system. This system can be provided by the anchoring member due to the shape of the anchoring member as described above (i.e., tubular anchor member) or a retention member can be provided. For example the retention member may include a positive mechanical connection on a surface of the anchor member opposite the patient interface 140. The positive mechanical connection may include a slide track with a locking position, a press fit connection, or some other latching type connection. In another alternative, a magnetic connection between the probe 104 and the anchoring member can also be provided. In yet another alternative, a retention member may be in the form of a strap system provided to secure the probe 104 to the anchoring member. The strap system can be a system of elastic straps, a belt type system, a pair of hook and loop type straps or other strap securing system 102.

Referring again to FIG. 10, the probe 104 connecting system can include one or more straps 146 adapted to sleevably receive the probe 104. The straps 146 extend from the anchoring member and are connected on each end to the anchoring member. In some embodiments, the straps 146 can be elastic straps and the length of the unstretched strap 146 can be less than the peripheral dimension of the probe 104 less the lateral dimension of the interfacing surface 110 of the probe 104. As such, when the probe 104 is inserted into the patch 142, the strap 146 can stretch and resist dislodgement of the probe 104. In another embodiment, the straps 146 are a more resilient material and slots can be provided on the housing 106 of the probe 104 opposite the interfacing surface 110. As such, when the probe 104 is inserted into the patch 142, the straps 146 can slip into the slots preventing the probe 104 from moving freely from the patch 142. In still other embodiments, the straps 146 can additionally or alternatively include a hook and loop surface corresponding to a hook and loop surface positioned on the probe 104. As such, once inserted the probe 104 can be retained therein by the securing restraint of the hook and loop connection to the straps 146.

As further shown in FIG. 10, the securing system 102 can include an opening 118 to accommodate the image mechanism of the probe 104. As such, the securing system 102 can be sized and dimensioned to fit the probe 104 so as to allow the image mechanism to align with the opening 118 in the securing system 102. In some embodiments, an ultrasonic gel can be provided to assure continual contact between the imaging mechanism and the probe 104. In other embodiments, the opening 118 may be filled with a material conducive to transmitting ultrasonic signals. For example, the material may be a gel filed material or other material having a density similar to the human body.

Regarding the probe 104 recognition module, the securing system 102 can include a module adapted to recognize the presence of a probe 104 and further act as a protection device against unauthorized or inadvertent usage of the probes 104. In some embodiments, the recognition module can include an embedded electronic computerized chip used to communicate with the control module of the probe 104. The chip 148 can include, for example, a code or other protection system to assure proper placement and use of the probe 104. In some embodiments, the chip may include a calibration protocol that performs a calibration on the probe 104 upon attachment of the probe 104 to the securing system 102. In other embodiments, the recognition module includes a bar code readable by an optical eye on the probe 104. In still other embodiments, the recognition module may include electrical contacts on the securing system 102 wherein the electrical circuit is completed when a probe 104 is attached. In still other embodiments, the recognition module can include a wireless type communication between the securing system 102 and the probe 104, such as, for example, radio frequency, Wi-Fi, or blue tooth type receiver and/or transmitter.

Having described the device depicted in FIGS. 3-11 in great detail, additional probe 104 embodiments will now be disclosed with a focus on alternative embodiments of a base structure and an adjustment mechanism and the relationships therebetween.

Figure 12:
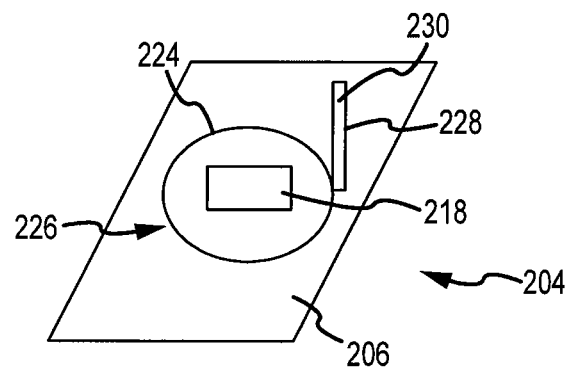
FIG. 12 shows a schematic view of a probe according to certain embodiments.

Referring to FIG. 12, a probe 204 is shown where the base structure is in the form of a platform 206. The platform 206 may be rigid, flexible and or moldable and may be connected to a securing system 202. The platform 206 may include a fixed outer edge and an adjustment mechanism may include a rotating circular inner edge 224, a movement mechanism 226, and at least one lateral sidebar 228.

The fixed outer edge of the platform 206 can interface with the securing system 202 and can allow the circular inner edge to rotate up to 360°. The rotating inner edge 224 of the platform 206 has a central opening 218 allowing the image mechanism to be inserted therein. The shape of the central opening 218 may be adjustable to fit with the shape of the image mechanism. The movement mechanism 226 permitting the inner edge 224 of the platform 206 to rotate within the fixed outer edge may be a track system, a rail system, a friction-based system or a ball-bearing system. The lateral sidebar 228 interfaces with the lateral side of the image mechanism using a male-female pin system 230. One or more sidebars 228 may be used. Each sidebar 228 may be a continuous piece or a fenestrated piece that permits height adjustments. The sidebar 228 allows the image mechanism to be adjusted according to an elevation plane in relations to the patient's body surface. Once optimally positioned, the sidebar male-female pin 230, the sidebar height adjustment and the rotating inner edge 224 may be locked in place. The locking mechanism may be an overhead clip, individual tight screw systems or any other locking systems that would allow the distal chamber to be locked in place. This embodiment can be manually adjusted through the use of the sidebar and rotation of the movement mechanism.

Figure 13:
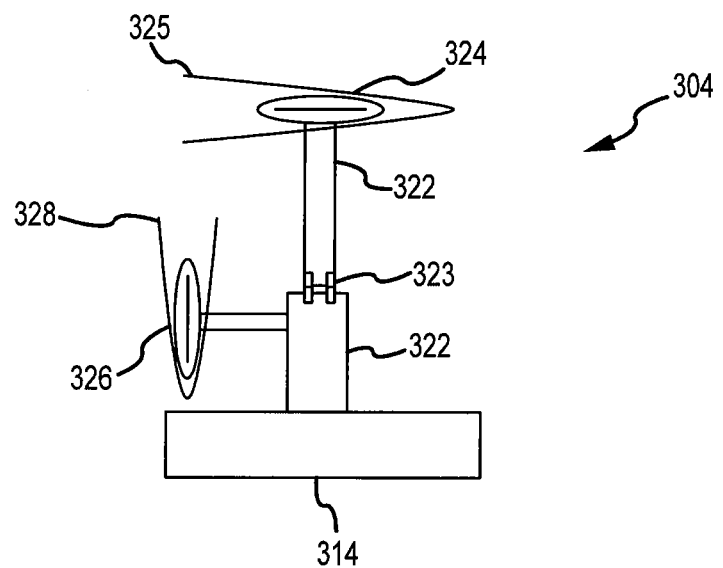
FIG. 13 shows a schematic view of a probe according to certain embodiments.

Referring now to FIG. 13, a schematic diagram of a probe 304 is shown. The adjustment mechanism of the probe 304 may be built inside a housing 306 similar to that described above: The mechanism can include a rotatable platform 314, a driving shaft 322, an elevation hinge 323, a rotation pulley or a screw 324, an elevation pulley or a screw 326, and control cables 325, 328.

The image mechanism of the probe 304 can be mounted on the internal rotatable platform 314. The platform 314 can rotate 360 degrees. The driving shaft 322 can be attached distally to the midline portion of the rotatable platform 314 and proximally to the rotation pulley or the screw mechanism 324. The rotation pulley or screw 324 can have a lateral groove where the control cable 325 can be inserted. The driving shaft 322 can also have an elevation hinge 323 that allows the rotatable platform 314 to be flexed forward and backward. The elevation hinge 323 can be connected to an elevation pulley or a crew 326. The elevation pulley or the screw 326 and the control cable 328 can allow the hinge 323 to be flexed to the desired elevation angle. The pulleys 324, 326 and control cables or screw mechanisms 325, 328 may be attached to manually controlled knobs or an electrical motor and controls.

Figure 14:
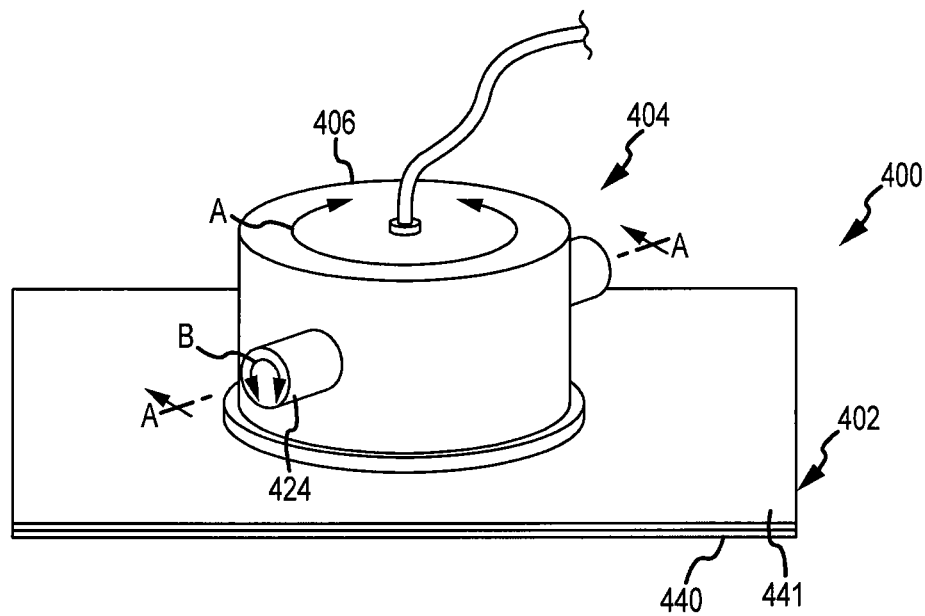
FIGS. 14 and 15 show a device including a probe and a securing system according to certain embodiments.
Figure 15:
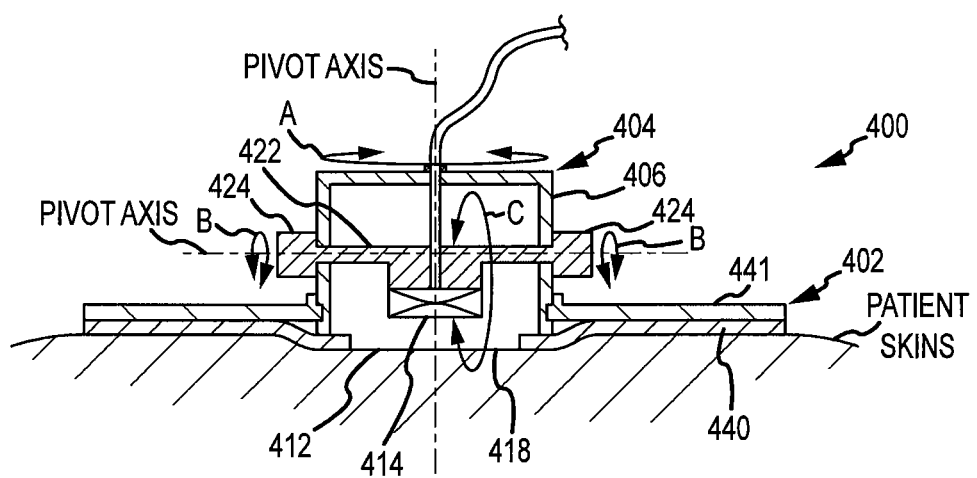

Referring now to FIGS. 14 and 15, wherein FIG. 15 is a view of section A-A cut on FIG. 14, another embodiment of a device 400 including a probe 404 and a securing system 402 is shown. In this embodiment, a securing system 402 in the form of a patch assembly can be provided and a housing 406 can be movably affixed thereto to form an adjustment mechanism. The patch assembly may have a flexible lower adhesive layer 440 for affixing the probe 404 to the patient skin surface and an upper base layer 441. The adjustment mechanism may include a housing 406 rotatably coupled to the base layer 441 in such a manner that allows the housing 406 to rotate in a plane generally parallel to the base layer 441, as indicated by arrows A in FIGS. 14 and 15. A tilt mechanism 422, which may include knobs 424, extends through the housing 406 having a pivot axis generally parallel to the base layer 441 and generally perpendicular to a pivot axis of the housing 406, which is generally perpendicular to the base layer 441. A transducer 414 may be supported off of the tilt mechanism 422 and may be formed of a single piezoelectric crystal or any one or more of the above-mentioned arrays. The tilt mechanism 422 may be caused to pivot about its pivot axis, as indicated by arrows B, to allow the transducer 414 to be swung or pivoted as indicated by arrow C. A conductor wire 408 may extend from the transducer 414 and out the housing 406 to an interface 490 similar to that shown in FIGS. 7 and 9. The housing 406 may be rotated about its pivot axis and the tilt mechanism 422 may be pivoted about its pivot axis. As a result of its two perpendicular pivot axes, the adjustment mechanism may be affixed to a patient and then the transducer 414 may be oriented as needed by pivoting the tilt mechanism 422 and the housing 406 about their respective pivot axes as needed. While the housing 406 and knobs 424 may be physically grasped to bring about the desired pivoting of the housing 406 and the tilt mechanism 422, motorized or other powered means may be employed on the adjustment mechanism to make the desired pivoting automated, in a manner similar to that discussed with respect to FIG. 13. The interaction between the tilt mechanism 422 and the housing 406 and between the housing 406 and base 441 may be a ratchet type interaction such that the tilt mechanism 422 and housing 406 stay in place once set in a position. The base 441 and housing 406 may each include respective openings 418, 412 corresponding to the location of the transducer 414.

Figure 16A:
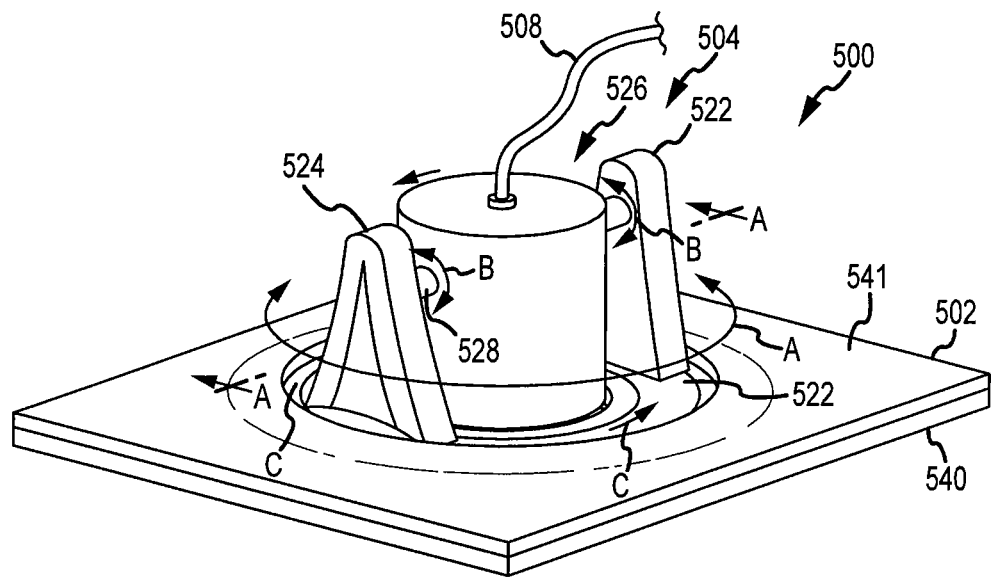
FIGS. 16a-b and 17 show a device including a probe and a securing system 102 according to certain embodiments.
Figure 16B:
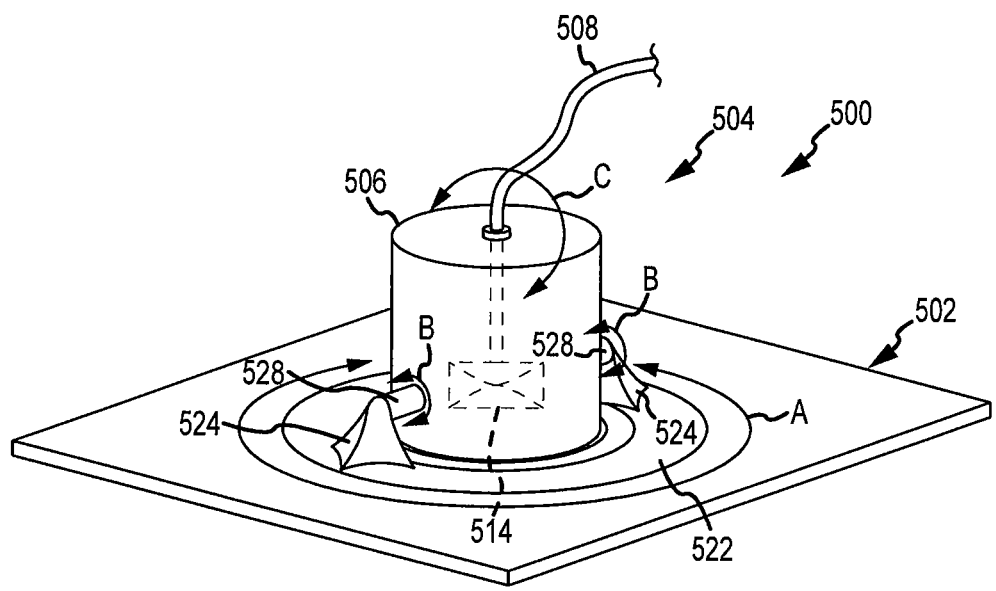
Figure 17:
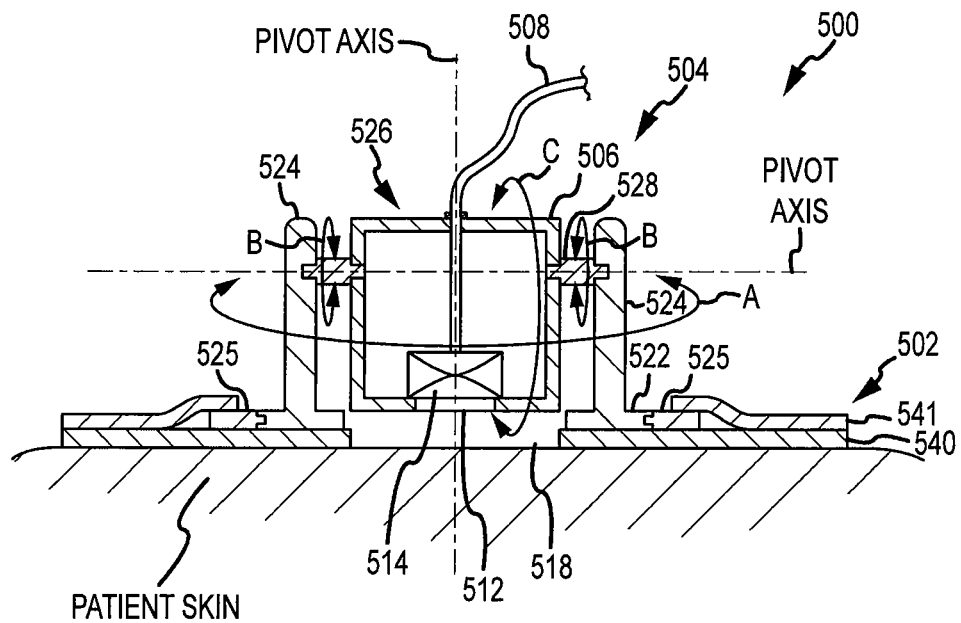

Referring now to FIGS. 16 and 17, wherein FIG. 17 is a cross-sectional view A-A cut on FIG. 16, another embodiment of a device 500 with a probe 504 and a securing system 502 can be seen. In this embodiment, device 500 may include a securing system 502 in the form of a patch assembly and a probe 504. The patch assembly may have a flexible lower adhesive layer 540 for affixing the probe 504 to the patient skin surface and an upper base layer 541. The probe 504 may include a ring 522 rotatably coupled to a portion 525 of the base layer 541 in such a manner that allows the ring 522 to rotate in a plane generally parallel to the base layer 541, as indicated by arrows A in FIGS. 16a and 17, the ring 522 forming a portion of an adjustment mechanism. One or more arms 524 may extend upward from the ring 522 to pivotally support a tilt mechanism 526, which may include a housing 506 that is pivotally supported from the arms 524 via axles or pivot pins 528, the tilt mechanism 526 forming another portion of the adjustment mechanism. Thus, the tilt mechanism 526 has a pivot axis generally parallel to the base layer 541 and generally perpendicular to a pivot axis of the ring 522, which is generally perpendicular to the base layer 541. An transducer 514 may be supported off of the housing 506 of the tilt mechanism 526 and may be formed of a single piezoelectric crystal or any one or more of the above-mentioned arrays. The tilt mechanism 526 may be caused to pivot about its pivot axis, as indicated by arrows B, to allow the transducer 514 to be swung or pivoted as indicated by arrows C. A conductor wire 508 may extend from the transducer 514 and out the housing 506 to an interface 590 similar to that described with respect to FIGS. 7 and 9. The ring 522 may be rotated about its pivot axis and the tilt mechanism 526 may be pivoted about its pivot axis. As a result of its two perpendicular pivot axes, the device 500 may be affixed to a patient and then the transducer 514 may be oriented as needed by pivoting the tilt mechanism 526 and the housing 506 about their respective pivot axes as needed. While the arms 524 and housing 506 may be physically grasped to bring about the desired pivoting of the ring 522 and the tilt mechanism 526, motorized or other powered means may be employed on the device 500 to make the desired pivoting automated, in a manner similar to that discussed with respect to FIG. 13. The interaction between the tilt mechanism 526 and the ring 522 and between the housing ring 522 and base 541 may be a ratchet type interaction such that the tilt mechanism 526 and ring 522 stay in place once set in a position. The base 541 and housing 506 may each include respective openings 518, 512 corresponding to the location of the transducer 514. While the pivot axis of the tilt mechanism 526 may be near the top of the housing 506, as indicated in FIGS. 16a and 17, in other embodiments, the pivot axis of the tilt mechanism 526 may be in other locations, such as, for example, the near the bottom of the housing 506, as depicted in FIG. 16b.

Figure 18:
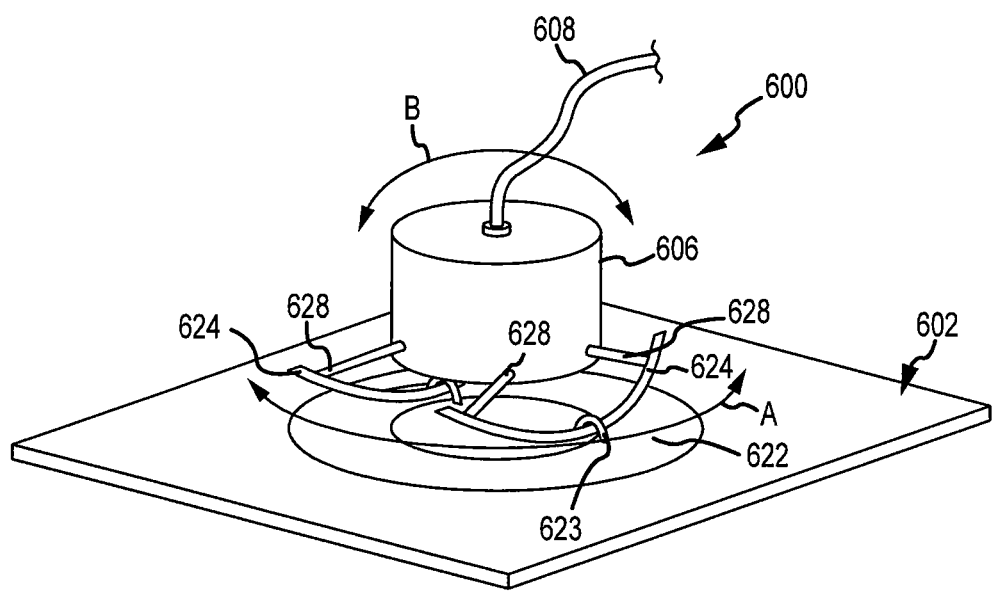
FIGS. 18 and 19 show a device including a probe and a securing system according to certain embodiments.
Figure 19:
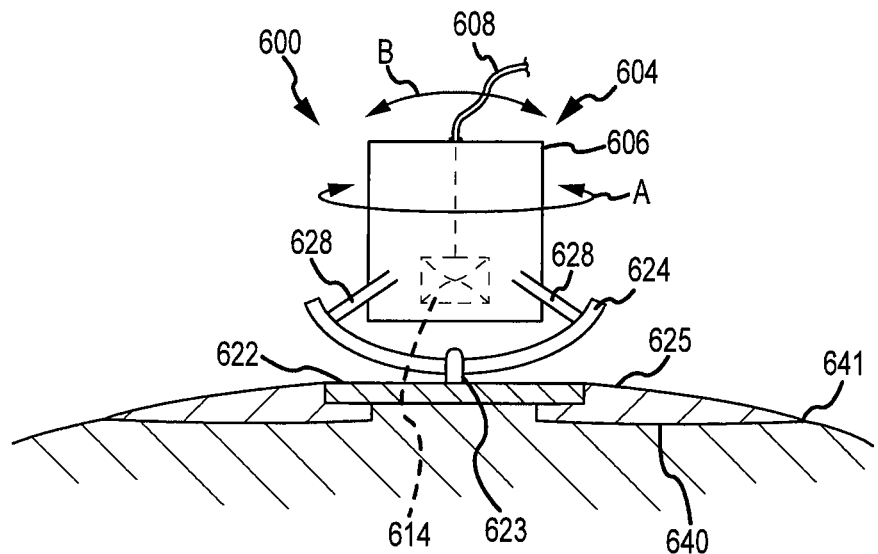

Referring now to FIGS. 18 and 19, yet another embodiment of a device 600 is shown. As shown the device 600 may include a securing system 602 in the form of a patch assembly and may also include a probe 604 attached to the securing system 602. The patch assembly may have a flexible lower adhesive layer 640 for affixing the device to the patient's skin surface and an upper base layer 641. The probe 604 may include a ring 622 rotatably coupled to a portion 625 of the base layer 30 in such a manner that allows the ring 622 to rotate in a plane generally parallel to the base layer 641, as indicated by arrows A in FIGS. 18 and 19, the ring 622 forming a portion of the adjustment mechanism. One or more loops 623 may extend upward from the ring 622 to slideably receive rocker members 624 that are supported off of a transducer housing 606 via arms 628 such that the rocker members 624 may slide through the loops 623 causing the housing 606 to tilt as indicated by the arrow B due to the arc shape of the rocker members 624, the loops 623 and slidable rocker members 624 forming another portion of the adjustment mechanism. Thus, the housing 606 has a pivot axis generally parallel to the base layer 641 and generally perpendicular to a pivot axis of the ring 622, which is generally perpendicular to the base layer 641. A transducer 614 may be supported off of the housing 606 and may be formed of a single piezoelectric crystal or any one or more of the above-mentioned arrays. The housing 606 may be caused to pivot about its pivot axis, as indicated by arrows B, to allow the transducer 614 to be swung or pivoted. A conductor wire 608 may extend from the transducer 614 and out the housing 606 to the and interface 690 similar to that shown in FIGS. 7 and 9. The ring 622 may be rotated about its pivot axis and the housing 606 may be pivoted about its pivot axis. As a result of its two perpendicular pivot axes, the device 600 may be affixed to a patient and then the transducer 614 may be oriented as needed by pivoting the housing 606 and the ring 622 about their respective pivot axes as needed. While the ring 622 and housing 606 may be physically grasped to bring about the desired pivoting of the ring 622 and the tilt housing 606, motorized or other powered means may be employed on the mechanism to make the desired pivoting automated, in a manner similar to that discussed with respect to FIG. 13. The interaction between the arc-shaped rocker members 624 and the loop 623 and between the ring 622 and base 641 may be a ratchet type interaction such that the tilt housing 606 and ring 622 stay in place once set in a position. In a manner similar to that discussed above, the base 641 and housing 606 may each include respective openings 618, 612 corresponding to the location of the transducer 614.

Figure 20:
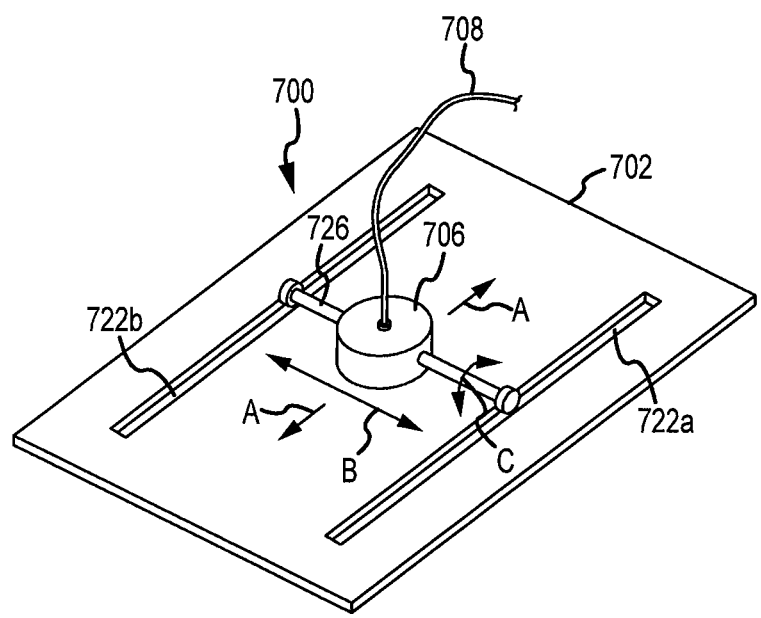
FIG. 20 shows a device including a probe and a securing system according to certain embodiments.

Referring to FIG. 20, yet another embodiment of a device 700 is shown. The device 700 may include a securing system 702 in the form of a patch assembly similar to those discussed above. The device 700 may also include a probe 704 having an adjustment mechanism in the form of a pair of parallel rails 722a, 722b, a traveling rail 726, and a housing 706. The opposite ends of the traveling rail 726 may be configured to displace along the parallel rails 722a, 722b as indicated by arrows A. The housing 706 may be configured to both slide along the traveling rail 726, as indicated by arrow B, and pivot about the traveling rail 726, as indicated by arrow C. As with the housings 706 discussed above, a transducer 714 may be located in the housing 706 as discussed above. The rail arrangement and pivoting of the housing 706, as can be understood from arrows A, B and C allows the housing 706 to be positioned as desired to allow the transducer 714 to be aimed as desired. The housing 706 may be grasped manually to position it as desired; alternatively, the mechanism may be powered for automated displacement and positioning of the housing 706.

Figure 21:
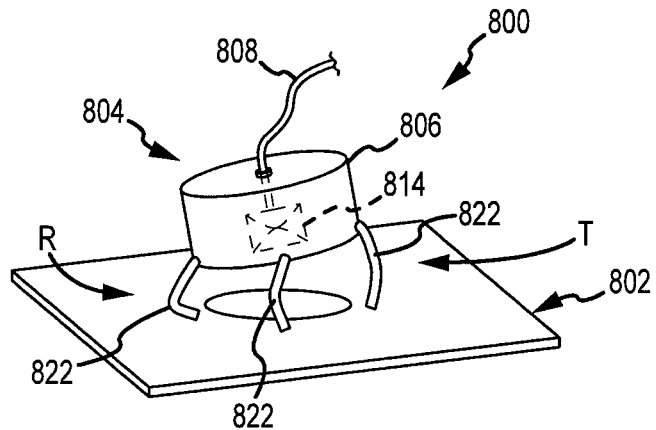
FIG. 21 shows a device according to certain embodiments.

Referring now to FIG. 21, yet another embodiment of a device 800 is shown. The device 800 may include a securing mechanism 802 in the form of a patch assembly and may further include a probe 804 with a housing 806, a transducer 814 and cable 808 similar to those discussed above. However, instead of being pivotally coupled to the patch assembly, the housing 806 may be coupled to the patch assembly via an adjustment mechanism in the form of multiple deformable arms 822. These arms 822 may be formed of a flexible material that retains a shape the arms 822 are deformed into until physically caused to assume a new shape. Thus, the housing 806 may be displaced to cause the arms 822 to deform or deflect into a new shape that facilitates the transducer 814 being positioned as desired, the arms 822 maintaining the housing 806 in the desired position until acted upon. As can be understood from FIG. 20, the arms 822 may be bent on a side as indicated by arrow R, the arms 822 on the other side (indicated by arrow T) being in a non-bent configuration. As a result, the housing 806 is tipped relative to the patch assembly, thereby allowing the transducer 814 to be oriented as desired.

Figure 22:
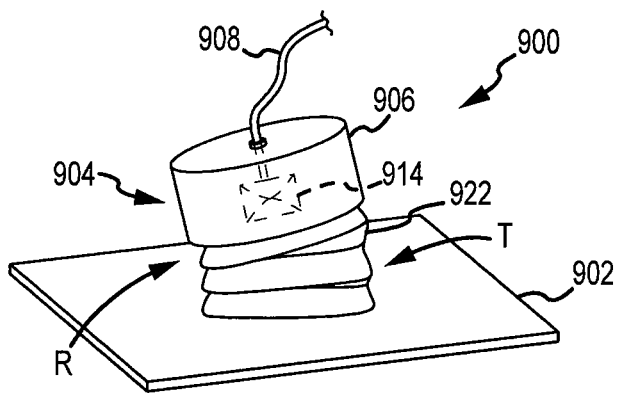
FIG. 22 shows a device according to certain embodiments.

Referring now to FIG. 22, still another embodiment of a device 900 is shown. The device 900 may be configured to operate in a manner similar to that depicted in FIG. 21, except the adjustment mechanism shown in FIG. 21 as deformable arms 822 are replaced with an according or gusset style body 922 between the housing 906 and the patch. The accordion or gusset style body 922 may be formed of a flexible material that, in combination with its gusset shape, retains a deflection deformed into until physically caused to assume a new deflection. Thus, the housing 906 may be displaced to cause the gusset body 922 to deflect into a new shape that facilitates the transducer 914 being positioned as desired, the gusset body 922 maintaining the housing 906 in the desired position until acted upon. As can be understood from FIG. 22, the gusset body 922 may be compressed on a side as indicated by arrow R, the gusset body 922 on the other side (indicated by arrow T) being in a non-compressed or even extended configuration. As a result, the housing 906 is tipped relative to the patch assembly, thereby allowing the transducer 914 to be oriented as desired.

Figure 23:
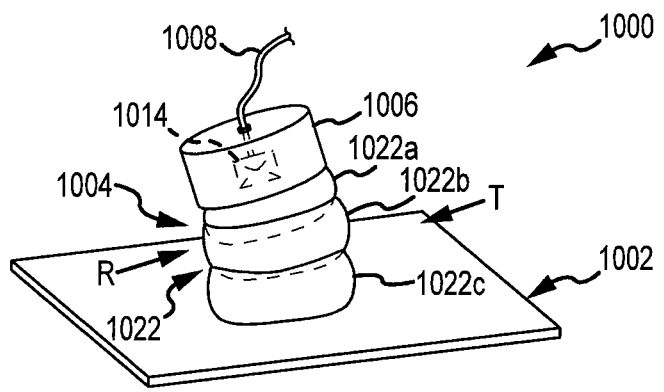
FIG. 23 shows a device according to certain embodiments.

Referring now to FIG. 23, still another embodiment of a device 1000 is shown. The device 1000 may be configured to operate in a manner similar to that depicted in FIG. 22, except the adjustment mechanism is in the form of a gusset body 922 of FIG. 22 is replaced with a segmented body 1022 formed of multiple semi-hemispherical bodies 1022a, 1022b, 1022c interlocked and received within each other in a manner similar to that found with a lamp having a flexible neck extending between the lamp's base and head. As indicated by the dashed lines in FIG. 23, the bodies 1022a, 1022b, 1022c may be tipped within each other to allow the segmented body 1022 to assume a shape and thereby position the housing 1006 until the segmented body 1022 is acted on to assume another deflected condition. Thus, the housing 1006 may be displaced to cause the segmented body 1022 to deflect into a new shape that facilitates the transducer 1014 being positioned as desired, the segmented body 1022 maintaining the housing 1006 is the desired position until acted upon. As can be understood from FIG. 23, the segmented body 1022 may be tipped on a side so the bodies 1022a, 1022b, 1022c are received in each other to a greater extent as indicated by arrow R, the bodies 1022a, 1022b, 1022c on the other side (indicated by arrow T) being in a less received state relative to each other. As a result, the housing 1006 is tipped relative to the patch assembly, thereby allowing the transducer 1014 to be oriented as desired.

Although the present disclosure has been described with reference to various embodiments, persons skilled in the art will recognize that changes may be made in form and detail without departing from the spirit and scope of the invention. The techniques of this disclosure may be embodied in a wide variety of devices or apparatuses. Any components, modules, or units have been described to emphasize functional aspects and does not necessarily require realization by different hardware units, etc.

Accordingly, the techniques embodied/described herein may be implemented in hardware, software, firmware, or any combination thereof. Any features described as modules or components may be implemented together in an integrated logic device or separately as discrete but interoperable logic devices. If implemented in software, the techniques may be realized at least in part by a computer-readable medium comprising instructions that, when executed, performs one or more of the methods described herein. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

If implemented in software, the software code may be initially stored on a computer readable medium, and may be executed by one or more processors, such as one or more digital signal processors (DSPs), general purpose microprocessors, an application specific integrated circuits (ASICs), field programmable logic arrays (FPGAs), or other equivalent integrated or discrete logic circuitry. The term "processor," as used herein may refer to any of the foregoing structure or any other structure suitable for implementation of the techniques described herein. In addition, in some aspects, the functionality described herein may be provided within dedicated software modules or hardware modules configured for encoding and decoding, or incorporated in a combined video codec. Also, the techniques could be fully implemented in one or more circuits or logic elements.

Many other aspects of this disclosure will become apparent from the teaching above. Nothing in this disclosure should be construed as any admission regarding prior art or known systems. Any discussion of background material is provided for context, and does not necessarily mean that such background material was known, or that problems akin to background material were known.

What is claimed is:

1. A device for acquiring ultrasound-generated data from a patient, the device comprising:
 a securing system having an anchor; and
 a probe configured for connection to the securing system, the probe comprising:
  a base having an interfacing surface;
  an imaging mechanism having an ultrasound transducer, the imaging mechanism being adjustable relative to the base and configured to send and receive ultrasound signals along an imaging direction; and an adjustment mechanism configured to adjust the imaging mechanism relative to the base thereby adjusting the imaging direction, the adjustment mechanism comprising:

a first adjustment mechanism configured to adjust the imaging mechanism about a first axis orthogonal to the interfacing surface, the first adjustment mechanism comprising an annular ring oriented parallel to and offset from the interfacing surface and having an orientation actuator having a motor, the orientation actuator operably coupled thereto for pivoting the imaging mechanism about the first axis; and a second adjustment mechanism configured to adjust the imaging mechanism about a second axis parallel to the interfacing surface, the second adjustment mechanism comprising a gear extending from the imaging mechanism and being positioned orthogonal to the interfacing surface and having a direction actuator having a motor, the direction actuator operably coupled thereto for pivoting the imaging mechanism about the second axis.

2. The device of claim 1, wherein the base includes a housing and the imaging mechanism is pivotally and rotatably positioned within the housing.

3. The device of claim 1, wherein the base includes a frame and the imaging mechanism is pivotally positioned on the frame.

4. The device of claim 1, wherein the imaging mechanism is positioned within the annular ring and supported by a pivot pin extending parallel to the interfacing surface.

5. The device of claim 1, wherein the securing system further comprises a connection system positioned on the anchor and configured for removably attaching the probe.

6. The device of claim 1, wherein the anchor includes a patch including an adhesive membrane for adhesively connecting the securing system.

7. The device of claim 5, wherein the connection system includes at least a first retention member.

8. The device of claim 7 wherein the retention member includes a strap connected to the anchor at each end to form a retaining loop.

9. The device of claim 8, wherein the retention member is a hook and loop retention member.

10. The device of claim 9, wherein the probe includes a peripheral dimension and an unstretched length of the strap is less than the peripheral dimension less a width of the interfacing surface, wherein insertion of the probe within the strap causes the strap to stretch thereby securing the probe.

11. The device of claim 1, further comprising a recognition module configured to facilitate communication between the probe and the securing system.

12. The device of claim 11, wherein the recognition module includes a wireless communication link between the securing system and the probe.

13. The device of claim 11, wherein the recognition module includes a circuit, the circuit being open when the probe is not connected to the securing system and closed when the probe is connected to the securing system.

14. The device of claim 11, wherein the recognition module includes a calibration protocol stored within the securing system and adapted to calibrate the probe upon connection of the probe to the securing system.

* * * * *